US00RE50944E

(19) United States
(12) Reissued Patent
Gylleby et al.

(10) Patent Number: US RE50,944 E
(45) Date of Reissued Patent: Jul. 7, 2026

(54) MONITORING UNIT

(71) Applicant: SHL MEDICAL AG, Zug (CH)

(72) Inventors: Stefan Gylleby, Stockholm (SE); Daniel Säll, Segeltorp (SE)

(73) Assignee: SHL Medical AG, Zug (CH)

(21) Appl. No.: 18/124,700

(22) Filed: Mar. 22, 2023

Related U.S. Patent Documents

Reissue of:
(64) Patent No.: 10,980,943
Issued: Apr. 20, 2021
Appl. No.: 15/748,976
PCT Filed: Aug. 8, 2016
PCT No.: PCT/EP2016/068879
§ 371 (c)(1),
(2) Date: Jan. 30, 2018
PCT Pub. No.: WO2017/032586
PCT Pub. Date: Mar. 2, 2017

(30) Foreign Application Priority Data

Aug. 24, 2015 (EP) ..... 15182213
Feb. 24, 2016 (SE) ..... 1650240-3

(51) Int. Cl.
*A61M 5/20* (2006.01)
*A61M 5/315* (2006.01)
*A61M 5/31* (2006.01)

(52) U.S. Cl.
CPC ..... *A61M 5/20* (2013.01); *A61M 5/31566* (2013.01); *A61M 5/31568* (2013.01);
(Continued)

(58) Field of Classification Search
CPC ..... A61M 5/20; A61M 5/31566; A61M 5/31568; A61M 5/3157;
(Continued)

(56) References Cited

U.S. PATENT DOCUMENTS

2010/0137790 A1* 6/2010 Yodfat ..... A61M 5/14248 604/67
2011/0264033 A1* 10/2011 Jensen ..... A61M 5/486 604/93.01

(Continued)

FOREIGN PATENT DOCUMENTS

CN 101116077 A 1/2008
CN 102905613 A 1/2013

(Continued)

OTHER PUBLICATIONS

International Search Report and Written Opinion for Int. App. No. PCT/EP2016/068879, completed Oct. 25, 2016.

(Continued)

*Primary Examiner* — Catherine S Williams
(74) *Attorney, Agent, or Firm* — McDonnell Boehnen Hulbert & Berghoff LLP

(57) ABSTRACT

The present disclosure relates to a monitoring unit for a medicament delivery device, where the monitoring unit has a monitoring circuit arranged in the housing that is capable of detecting and monitoring functions of the medicament delivery device. The monitoring device also has an attachment mechanism provided arranged with releasable locking elements, a mechanical interface arranged to interact with a mating mechanical interface arranged on a medicament delivery device, and an activation switch arranged to activate said monitoring circuit.

27 Claims, 21 Drawing Sheets

(52) U.S. Cl.
CPC ... *A61M 5/3157* (2013.01); *A61M 2005/3126* (2013.01); *A61M 2005/3142* (2013.01); *A61M 2205/3375* (2013.01); *A61M 2205/3569* (2013.01); *A61M 2205/3584* (2013.01); *A61M 2205/3592* (2013.01); *A61M 2205/50* (2013.01); *A61M 2205/502* (2013.01); *A61M 2205/581* (2013.01); *A61M 2205/582* (2013.01); *A61M 2205/6045* (2013.01); *A61M 2205/6054* (2013.01); *A61M 2205/6063* (2013.01); *A61M 2205/6072* (2013.01); *A61M 2205/6081* (2013.01)

(58) Field of Classification Search
CPC .. A61M 2005/3126; A61M 2005/3142; A61M 2205/3375; A61M 2205/3569; A61M 2205/3584; A61M 2205/3592; A61M 2205/50; A61M 2205/502; A61M 2205/581; A61M 2205/582; A61M 2205/6045; A61M 2205/6054; A61M 2205/6063; A61M 2205/6072; A61M 2205/6081
See application file for complete search history.

(56) References Cited

U.S. PATENT DOCUMENTS

2011/0270214 A1* 11/2011 Jorgensen et al. ..... A61M 5/31551 604/500
2012/0004602 A1* 1/2012 Hanson ..... A61M 5/14248 604/67
2014/0005950 A1* 1/2014 Groeschke ..... A61M 5/31533 702/19
2014/0194825 A1 7/2014 Nielsen et al.
2015/0202376 A1 7/2015 Haupt

FOREIGN PATENT DOCUMENTS

| | | | | |
|---|---|---|---|---|
| CN | 103648561 | A | 3/2014 | |
| CN | 103702699 | A | 4/2014 | |
| CN | 104519930 | A | 4/2015 | |
| CN | 104918645 | A | 9/2015 | |
| EP | 3 256 193 | B1 | 11/2020 | |
| EP | 3 220 976 | B1 | 12/2024 | |
| JP | 2012-519027 | A | 8/2012 | |
| JP | 2014-516599 | A | 7/2014 | |
| JP | 2014-520584 | A | 8/2014 | |
| JP | 2015-509769 | A | 4/2015 | |
| KR | 2007-0105356 | A | 10/2007 | |
| KR | 2011-0041567 | A | 4/2011 | |
| WO | WO-2005053771 | A2 * | 6/2005 | ..... A61M 5/007 |
| WO | 2012/085031 | A1 | 6/2012 | |
| WO | 2012/127046 | A2 | 9/2012 | |
| WO | 2013/004844 | A1 | 1/2013 | |
| WO | 2013/120774 | A1 | 8/2013 | |
| WO | WO-2014020008 | A1 * | 2/2014 | ..... A61M 5/24 |
| WO | 2014/111337 | A1 | 7/2014 | |
| WO | 2014/128156 | A1 | 8/2014 | |
| WO | 2014/173771 | A1 | 10/2014 | |
| WO | 2015/121081 | A1 | 8/2015 | |

OTHER PUBLICATIONS

English Translation of Chinese Office Action for CN Application 2016800491439, dated Aug. 21, 2020.

* cited by examiner

MONITORING UNIT

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

*This is an application for reissue of U.S. Pat. No. 10,980,943, which issued on Apr. 20, 2021.*

The present application is a U.S. National Phase Application pursuant to 35 U.S.C. § 371 of International Application No. PCT/EP2016/068879 filed Aug. 8, 2016, which claims priority to European Patent Application No. 15182213.7 filed Aug. 24, 2015 and Swedish Patent Application No. 1650240-3, filed Feb. 24, 2016. The entire disclosure contents of these applications are herewith incorporated by reference into the present application.

TECHNICAL FIELD

The present disclosure relates to a monitoring unit to be arranged and operated in connection with a medicament delivery device, which monitoring unit is to be removably attached to the medicament delivery device.

BACKGROUND

With the growing use of self-medication units that are handled by the patients themselves, there is an increased desire for providing information to care givers such as physicians and nurses who need to know how the patients' treatment schemes are followed. Thus, there is an increased desire for monitoring the progress of the schemes, and in that respect, a number of medicament delivery devices have been provided with additional functionality in order to both monitor the use of a medicament delivery device, to store data from the monitoring as well as communicating the stored data to external devices for further processing of the monitored data.

One example is disclosed in the document WO 2014/128156. It comprises a medicament delivery device arranged with a logging module that is capable of detecting movement of components inside the medicament delivery device. According to one embodiment the logging module is arranged with a rotary sensor capable of counting the number of steps that a dial ring member is rotated relative to the fixed housing, both when a dose is set and when a dose is expelled.

The obtained number of steps from the rotary sensor may be used for different information purposes. For instance, the time of setting and expelling a dose may be registered such that the time elapsed since the last dose was administered may be calculated. Also the dose size may be obtained from the rotary sensor. The obtained data may then be transmitted to an external device such as a smartphone or the like. The preferred means of communication between the module and the smart phone is via NFC technology.

A drawback of the solution described above is that the module is an integrated part of the medicament delivery device. Since such a module comprises a number of components, rendering it rather expensive to manufacture, it is only suitable for a medicament delivery device that can be used a large number of times with replaceable medicament containers, a so-called re-usable medicament delivery device. It is not suitable for disposable medicament delivery devices that are discarded after use.

Another solution is disclosed in document WO 2014/020008. It comprises a supplementary device that is intended to be connected to a medicament delivery device comprising a housing having a mating unit that is configured to tightly but releasably embrace the housing of the medicament delivery device. The supplementary device is arranged with optical and acoustical sensors for gathering information from the medicament delivery device. The supplementary device further comprises a user interface for information input as well as displaying information. The supplementary device is designed to monitor handling of the device, such as the setting of a dose and/or injection of a dose by acoustic sensors. The supplementary device may communicate with a blood glucose monitoring system via communication technology such as Bluetooth.

Even though the housing preferably is designed to tightly embrace the housing of a certain medicament delivery device, the connection is not unique and the supplementary device may be connected to a number of medicament delivery devices that have similar housing dimensions. There is thus a risk that a user may use the supplementary device on another medicament delivery device than the one intended. It is therefore possible that the information obtained by the supplementary device is corrupted and cannot be trusted.

It would be advantageous if the medicament delivery device could be arranged with monitoring units that are more versatile but yet provide accurate and correct data from a medicament delivery device intended to be used with the monitoring unit.

SUMMARY

In the present application, the term "distal part/end" refers to the part/end of the device, or the parts/ends of the members thereof, which under use of the device, is located the furthest away from a delivery site of a patient. Correspondingly, the term "proximal part/end" refers to the part/end of the device, or the parts/ends of the members thereof, which under use of the device is located closest to the delivery site of the patient.

In the following description, the term "smart devices" will be used. In this context, smart devices may include electronic devices that are provided with processors that are capable of running computer programs, as well as comprising storage space to store programs and data retrieved from different external sources. It is further to be understood that the smart devices are provided with communication systems that are capable of communicating with data networks in order to access different databases. It is to be understood that databases may be accessed via the internet, so called cloud services, and/or databases that are connected directly to and accessed via local area networks. It is further to be understood that the smart devices in this context comprise some sort of human-machine interface for two-way communication. The human-machine interface may comprise displays, keyboards, microphones, loudspeakers, I/O-ports for connection of peripherals. Further, the smart devices may be provided with antennas for wireless communication with the networks. Also, the smart devices may be arranged with receiving and transmitting mechanisms capable of communicating with RFID/NFC tags, as well as programs capable of establishing and handling the communication with these tags. It is further to be understood that the smart devices may comprise near range communication technology such as RFID, NFC, Bluetooth, Ant, Zigbee, or the like.

The aim of the present disclosure is to remedy the drawbacks of the state of the art devices in this area of technology. This aim is solved by a monitoring unit comprising the features of the independent patent claim. Preferable embodiments form the subject of the dependent patent claims.

According to the present disclosure, it comprises a unit for monitoring a medicament delivery device. The monitoring unit preferably comprises a housing, with a monitoring circuit arranged in the housing. The monitoring unit is capable of detecting and monitoring functions of the medicament delivery device, which may be of many different types of functions, comprising removal of protective caps, penetration of an injection needle, start and/or end of a dose delivery sequence, shielding of an injection needle after withdrawal, just to mention a few.

The monitoring unit is preferably arranged with an attachment mechanism provided with a mechanical interface, which mechanical interface is arranged to interact with a mating mechanical interface arranged on a medicament delivery device, and an activation switch arranged to activate said monitoring circuit. The arrangement with mating interfaces enables a number of advantages. One advantage is that a firm connection may be obtained between the monitoring unit and the medicament delivery device at the same time as the monitoring unit may be detached and used on other medicament delivery devices. This has the advantage that the monitoring unit may be used with disposable medicament delivery devices that are discarded after use. The monitoring unit is then detached and attached to another medicament delivery device. The mating mechanical interfaces may also be arranged and designed with specific and unique features enabling only mating of specific monitoring units with specific medicament delivery devices. This may be important if a user has several treatment schemes involving different medicament delivery devices having different drugs, where specific monitoring units are to be connected to specific medicament delivery devices. There would be a pronounced risk of retrieving unreliable data if it was possible to connect a monitoring unit to any medicament delivery device.

According to one feasible solution, the medicament delivery device may be arranged with an activator element operably connected to a drive element of the medicament delivery device, wherein the drive element will force the activator element in a distal direction during the dose delivery sequence, acting on the activation switch. With this solution, the remaining force of the drive element will be utilized for activating the monitoring unit. In this respect, the activation switch may comprise at least one electrical switch operably arranged to activate the monitoring circuit. Thus, closing the switch will close a power circuit to the monitoring circuit, which will start the monitoring sequence.

There are a number of ways that the activation switch may be designed in order to provide information regarding the status and the operation of the medicament delivery device. For instance, the activation switch may be a vibration sensor arranged to detect vibrations generated when said medicament delivery device is operated. Vibrations may be generated by a number of components moving when the medicament delivery device is used, such as when a plunger rod has moved a stopper to an end of injection or when the activator element is released.

As an alternative, the activation switch may be a reed switch or a hall switch. Then the activator element may be arranged with a magnet arranged to be detected by the reed switch or the hall switch when the medicament delivery device is operated. The activator element and the switches are then arranged and oriented such that the magnet is positioned in the vicinity of them when for example an injection sequence has ended. It is however to be understood that the magnet may come in the vicinity of the switches at other sequences when the medicament delivery device is operated.

As a further alternative, the activation switch may be an opto switch arranged such that a light beam is broken when said medicament delivery device is operated. Also here, the activator element and the switch are arranged such that the activator element is positioned in the vicinity of the switch during a certain sequence of the medicament delivery device during use.

Other types of sensors may comprise capacitive proximity sensors or ultrasonic sensors. These types of sensors are capable of detecting actual movement of an activator element during operation of the medicament delivery device. The sensors then do not to be arranged so close to the activator element, providing more freedom when designing a monitoring unit.

The monitoring unit may be designed such that the activator unit may comprise further information that can be derived from the activation switch. This type of further information may be size of medicament container, type of medicament, strength of medicament, for example. One such information carrier may be a colour, wherein the activation switch may comprise an RGB colour sensor and wherein the activator element is provided with certain specific colours, where a specific colour is associated with certain information regarding the drug to be delivered.

Instead of a colour that is detectable, other types of patterns may be used, such as bar codes or QR codes, wherein the activation switch may be a bar code reader or a QR reader and wherein said activator element is arranged with a bar code or a QR code containing information regarding the drug to be delivered.

Another alternative in this regard is to use an RFID tag or an NFC tag, wherein the activation switch may be an RFID/NFC reader and wherein said activator element is arranged with an RFID/NFC tag containing information regarding the drug to be delivered.

In order to facilitate the connection between the monitoring unit and the medicament delivery device, the mechanical interface may comprise a number of flexible locking elements arranged to interact with mating locking elements of the medicament delivery device. Such a solution provides a good connection and, at the same time, a good release mechanism.

In that respect, the flexible locking elements may comprise tongues arranged with ledges, which ledges are arranged to engage ledges of the mating locking elements. Further, in order to increase the safety aspect regarding connecting the right monitoring unit with the right medicament delivery device, the mechanical interface may further comprise mechanical keying elements arranged with specific mechanical keying design.

According to one solution in that respect, the mechanical keying elements may comprise protrusions and recesses arranged in predetermined patterns. The mechanical keying elements may also comprise teeth. These protrusions and recesses may be used further in that the activation switch may be positioned such in said interface that it is mechanically activated by said protrusions. Then the protrusions may act directly on the activation switch for activating the monitoring unit such that the monitoring sequence starts.

Preferably the activation switch is arranged to be activated during operation of the medicament delivery device, and more preferably the activation switch is arranged to be activated during a dose delivery sequence.

According to one feasible solution, the medicament delivery device may be arranged with an activator element operably connected to a drive element of the medicament delivery device, wherein the drive element will force the activator element in a distal direction during the dose delivery sequence, acting on the activation switch. With this solution, the remaining force of the drive element will be utilized for activating the monitoring unit.

According to a further development of the disclosure, it may comprise a communication circuit operably arranged to transmit data to external data processing sources. In addition, the communication circuit is operably arranged to receive data from external data providing sources. With the solution, the monitoring unit is capable of transmitting monitored data for further processing such as monitoring treatment scheme adherence. The physician is then able to obtain information directly from the monitoring unit or via smart devices. He or she may then provide feedback or instructions to the user via the smart device or to the monitoring unit.

In connection with the latter aspect, the monitoring unit may further comprise a user communication circuit operably arranged to communicate data to a user. Thus, the data communicated to the user may be derived directly from the monitoring function of the monitoring unit as well as from data transmitted to the monitoring unit from external sources.

These and other aspects of, and advantages with, the present disclosure will become apparent from the following detailed description of the disclosure and from the accompanying drawings.

BRIEF DESCRIPTION OF DRAWINGS

In the following detailed description of the disclosure, reference will be made to the accompanying drawings, of which FIG. 1 exploded view of a medicament delivery device that may utilize a monitoring unit according to the present disclosure.

DETAILED DESCRIPTION

Figure 2A:
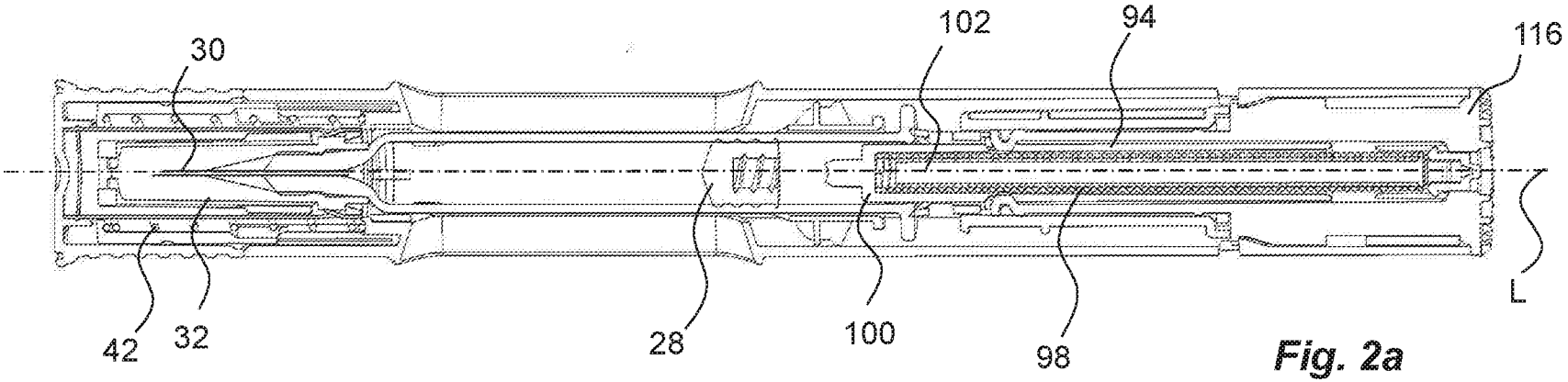
FIGS. 2-8 are detailed views of components comprised in the medicament delivery device according to FIG. 1.
Figure 2B:
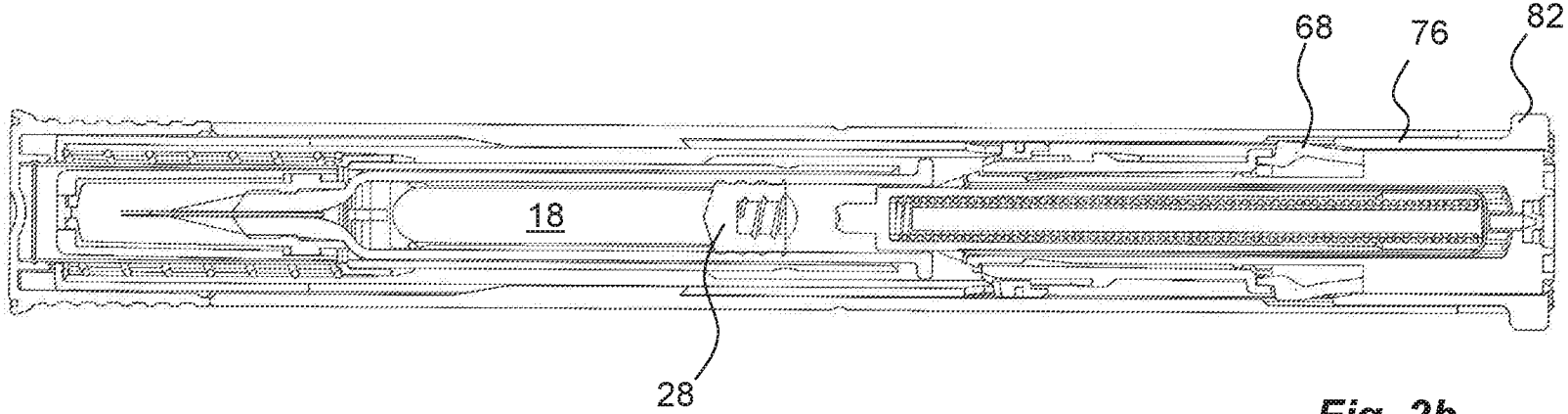
Figure 3:
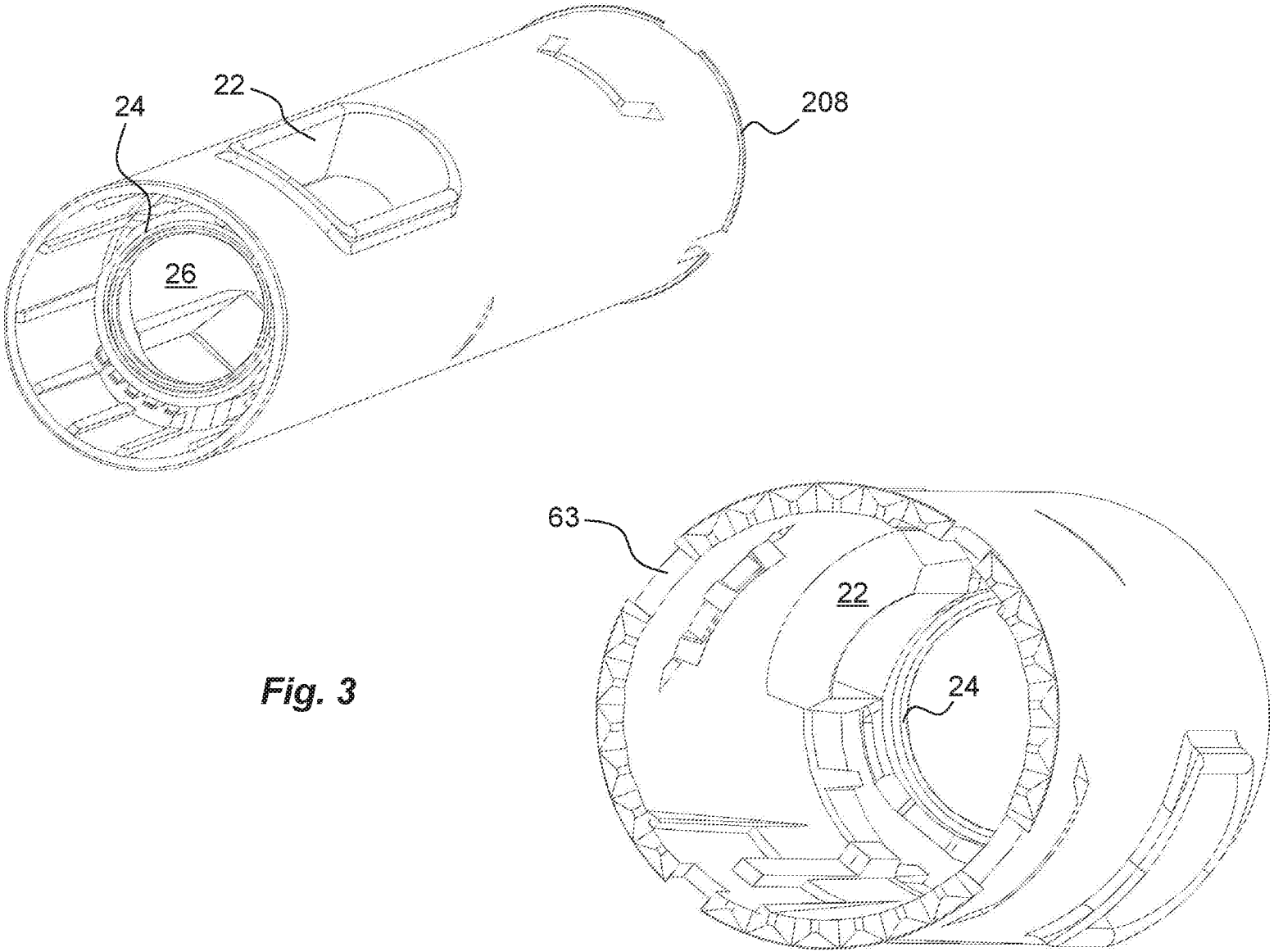

An example of a medicament delivery device that may be used with the present disclosure is shown in the drawings. It comprises a generally tubular elongated housing 10 having a distal end 12 and a proximal end 14, FIG. 1. The housing 10 is further arranged with openings or windows 16, through which a generally tubular medicament container 18 can be viewed. The medicament container 18 is placed in a medicament container holder 20. Each window 16 is further arranged with an inwardly directed ring-shaped circumferential ledge 22. As seen in FIG. 3, a support wall 24 is attached to the circumferential ledge 22, wherein the support wall 24 is arranged with a central passage 26. The edge of the central passage 26 as well as the inner edges of the circumferential ledges 22 of the windows 16 form support surfaces for the medicament container holder 20. The medicament container 18 is arranged with a movable stopper 28. The medicament container 18 has a proximal end on which a medicament delivery member 30, FIG. 2, is arranged, either made integral or connectable to the medicament container 18. The medicament delivery member 30 is preferably protected before use by a medicament delivery member shield 32 that in the embodiment shown is a so called rigid needle shield or RNS. It is however to be understood that other types of medicament delivery member shields may be used in order to obtain the desired protection of the medicament delivery member 30.

Figure 1:
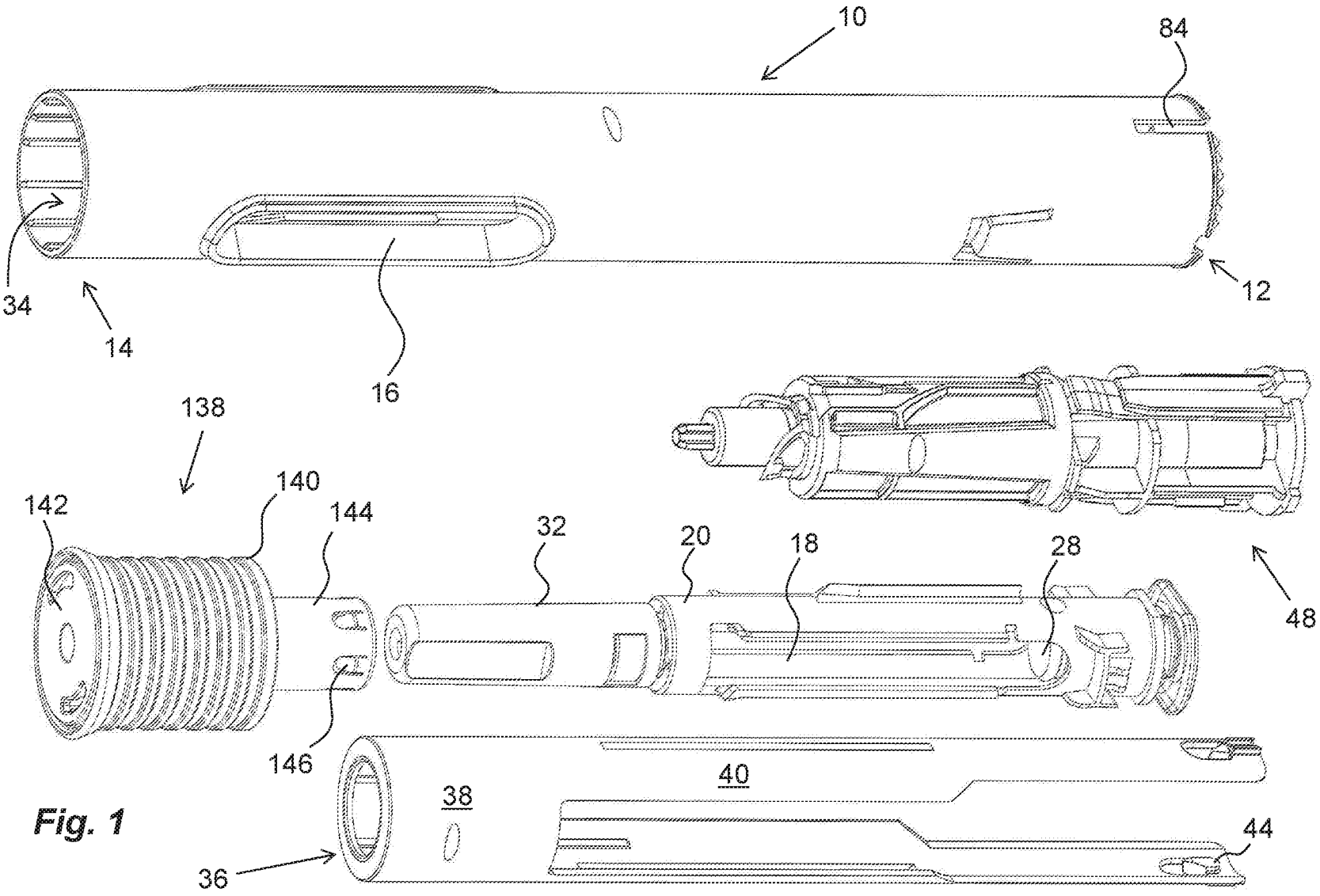

The proximal end of the housing is arranged with a central passage 34, FIG. 1, through which a generally tubular medicament delivery member guard 36 extends, FIG. 1. The medicament delivery member guard 36 comprises a proximal tubular part 38 and two distally directed arms 40 extending from the tubular part 38. A medicament delivery member guard spring 42, FIG. 2a, is arranged between a distally directed circumferential wall part of the medicament delivery member guard 36 and a proximally directed surface of the support wall 24. The arms 40 are arranged slidable along the medicament container holder 20. At the distal end of the arms 40, inwardly directed protrusions 44 are arranged, FIG. 1. The protrusions 44 are arranged to operably interact with a tubular rotator 46, FIGS. 4 and 5, of a drive unit 48.

The rotator 46 has a generally tubular shape and is arranged with guide ridges 50 that are intended to cooperate with the protrusions 44 of the medicament delivery member guard 36 as will be described, wherein some sections $\mathbf{50}_i$ of the guide ridges are inclined in relation to the longitudinal axis L of the device. A proximal part of the rotator 46 is further arranged with proximally directed tongues 52 adjacent the guide ridges, wherein the free ends of the tongues 52 are arranged with wedge-shaped outwardly directed protrusions 54, the function of which will be described below. The rotator 46 is further arranged with ledges 55 on its inner surface at a distal end, FIG. 5, providing a space 57 between the ledges in a circumferential direction.

Figure 4:
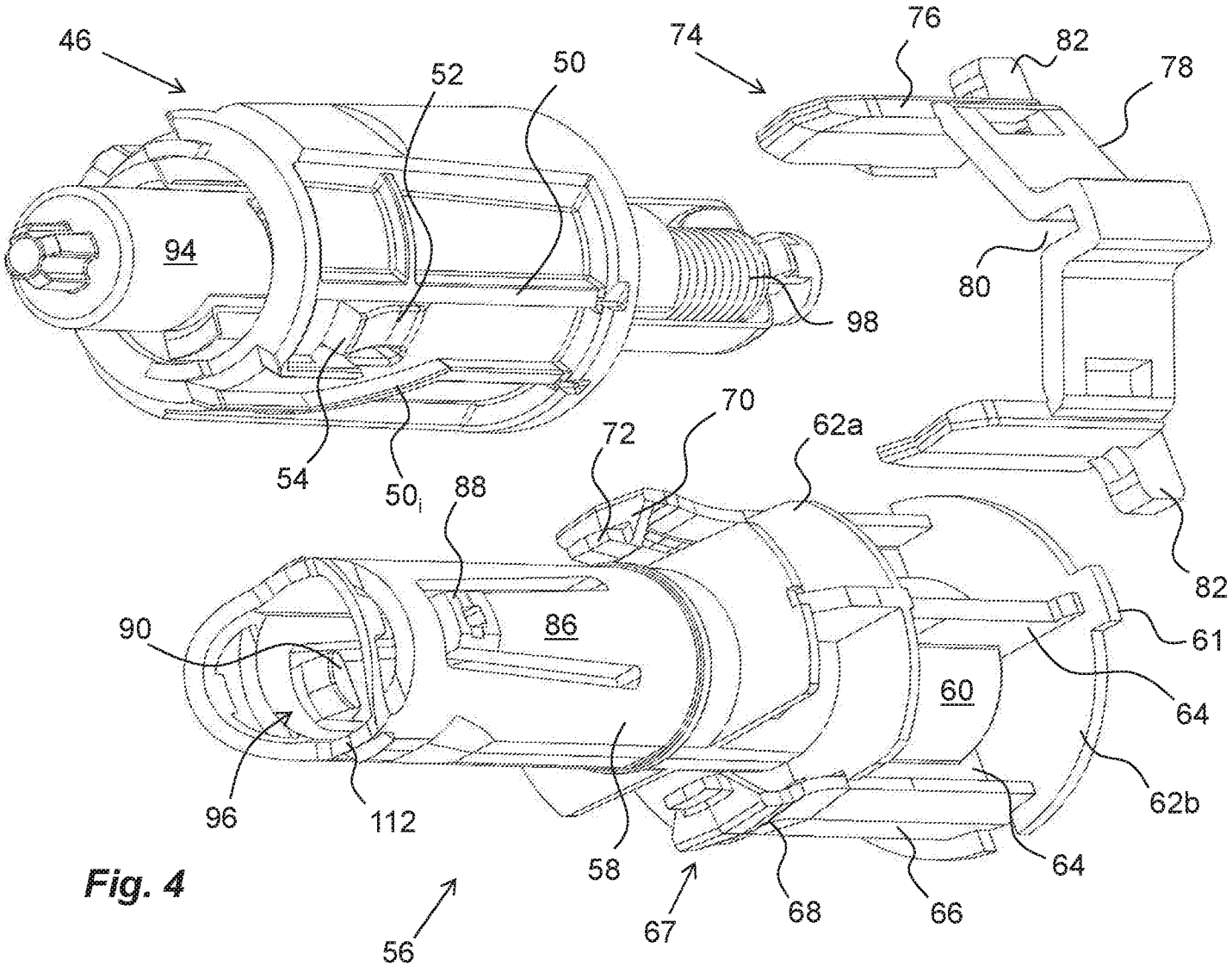
Figure 5:
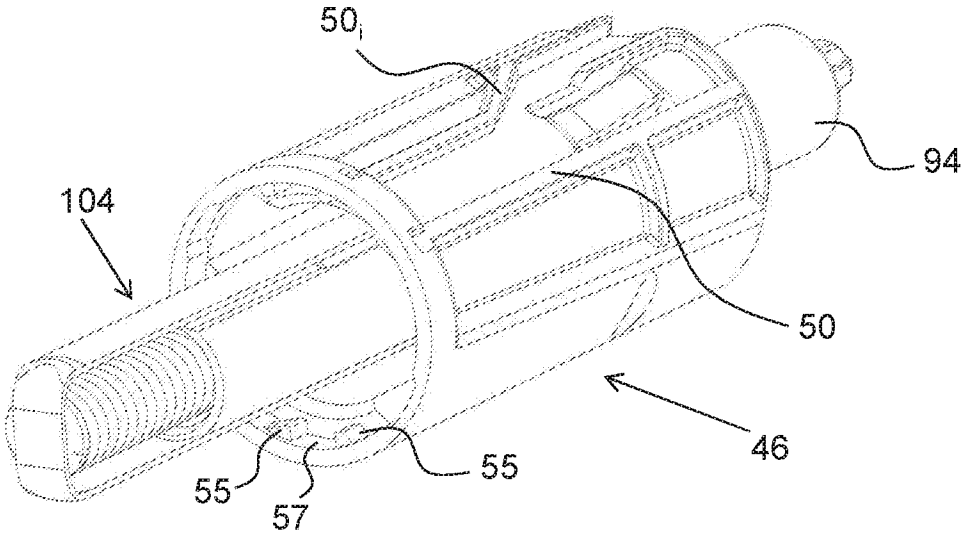

An actuator 56, FIG. 4, is further arranged operably to the rotator 46. It comprises a first proximal tubular section 58 having a diameter slightly smaller than the inner diameter of the rotator 46. It further comprises a generally tubular second section 60 arranged to fit into and to be attached to a distal part of the housing. The second section 60 is provided with two generally circular, radially extending, wall sections 62a, 62b. Four longitudinally extending wall sections 64 are arranged around the circumference of the second section 60 and extending between the radially extending wall sections 62a, 62b. The most distal of the wall sections 62b is arranged with radially outwardly directed protrusions 61 that fit into cut-outs 63 on a distal edge of the housing of the medicament delivery device. On two oppositely positioned longitudinal wall sections 64 extending between the radial wall sections 62, longitudinally extending ledges 66 are arranged. The ledges extend in the proximal direction with locking elements 67 that in the embodiment shown comprises tongue-shaped flexible sections 68 having a somewhat outwardly inclined direction. The ends of the tongue-shaped sections 68 are each arranged with an inwardly directed section 70. On each inwardly directed section 70 a proximally directed ledge 72 is arranged, the function of which will be explained below. In an initial position of the locking elements 67 in relation to the rotator 46, the ledges 72 fit into the spaces 57 between the ledges 55 of the rotator 46, thereby providing a rotational lock of said rotator 46.

A release element 74, FIG. 4, is further arranged to the second section 60 of the actuator 56. The release element 74 comprises two elongated plate-like members 76 interconnected by a bridge 78. The bridge 78 has a central longitudinally extending groove 80 which fits onto one of the longitudinally extending wall sections 64 whereby the plate-like members 76 are positioned radially outside the ledges 66. The release element 74 is then slidable in the longitudinal direction such that the proximal ends of the plate-like members 76 can affect the proximally directed tongue-shaped sections 68 of the locking element 67 as will be described. The plate-like members 76 are further arranged with radially outwardly directed protrusions 82, which protrusions 82 are arranged to fit into slits 84 in the housing 10 at the distal end thereof, FIG. 1.

The first section 58 is further arranged with proximally extending arms 86 that are arranged flexible in a generally radial direction. The free ends of the arms 86 have outwardly extending protrusions 88 that are to interact with inner surfaces of the rotator 46 as will be described. Further the free ends of the arms 86 are arranged with inwardly extending protrusions 90, which protrusions 90 are intended to interact with recesses 92 on a generally elongated plunger rod 94, FIG. 6. The protrusions 90 extend into a central passage 96 of the actuator 56, in which passage 96 the plunger rod 94 fits.

Figure 6:
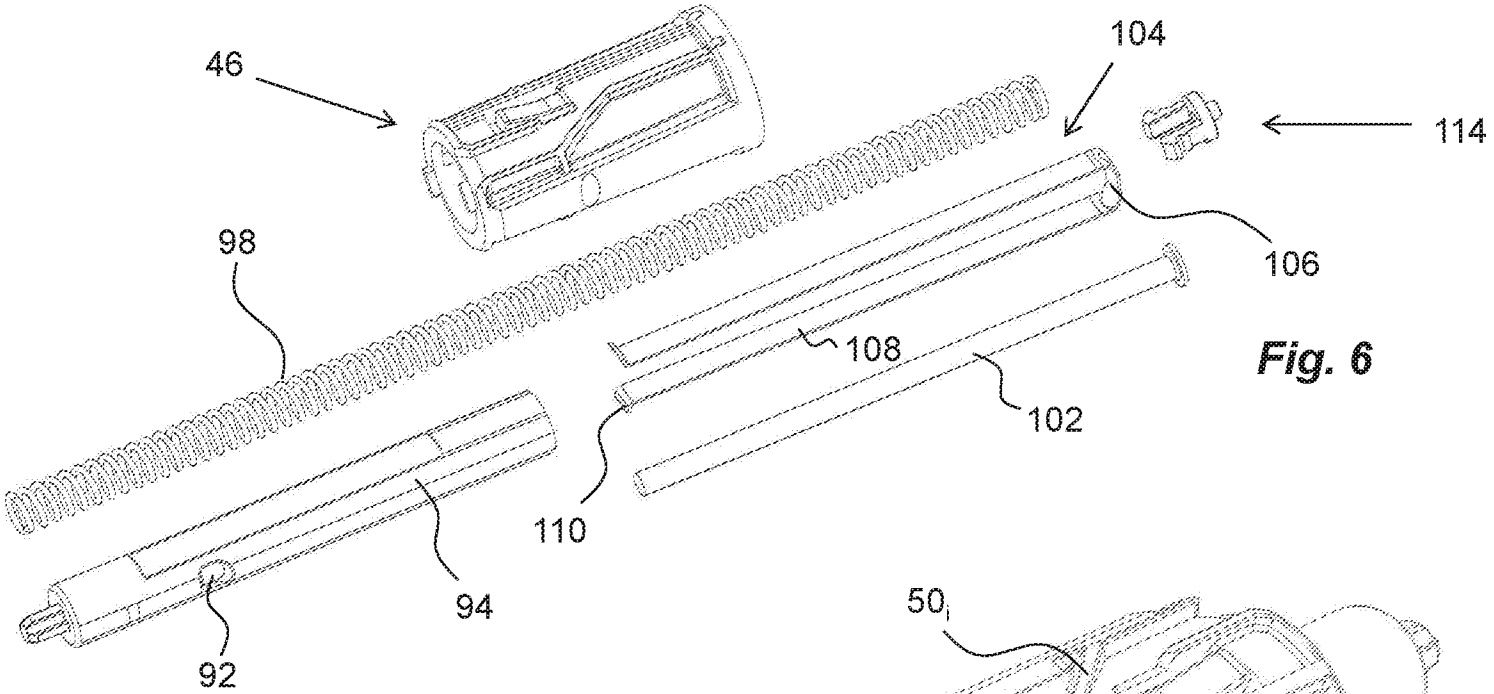

The drive unit 48 further comprises a drive spring 98, FIG. 6, that in the embodiment shown is placed inside a cavity of the hollow plunger rod 94, wherein the drive spring 98 is positioned with a proximal end thereof in contact with an end wall 100 of the plunger rod 94, FIG. 2. Inside the drive spring 98, a guide rod 102 is arranged. The distal end of the drive spring 98 is in contact with a generally U-shaped element, hereafter named activator 104, having a base 106 and two arms 108, FIG. 6. The arms 108 of the activator 104 are directed in the proximal direction along, and in contact with, the outer surface of the plunger rod 94, wherein the free ends of the arms 108 are arranged with generally radially outwardly directed ledges 110. These ledges 110 are arranged to be in contact with a proximally directed surface 112, FIG. 4, surrounding the central passage 96 of the actuator 56.

Figure 7:
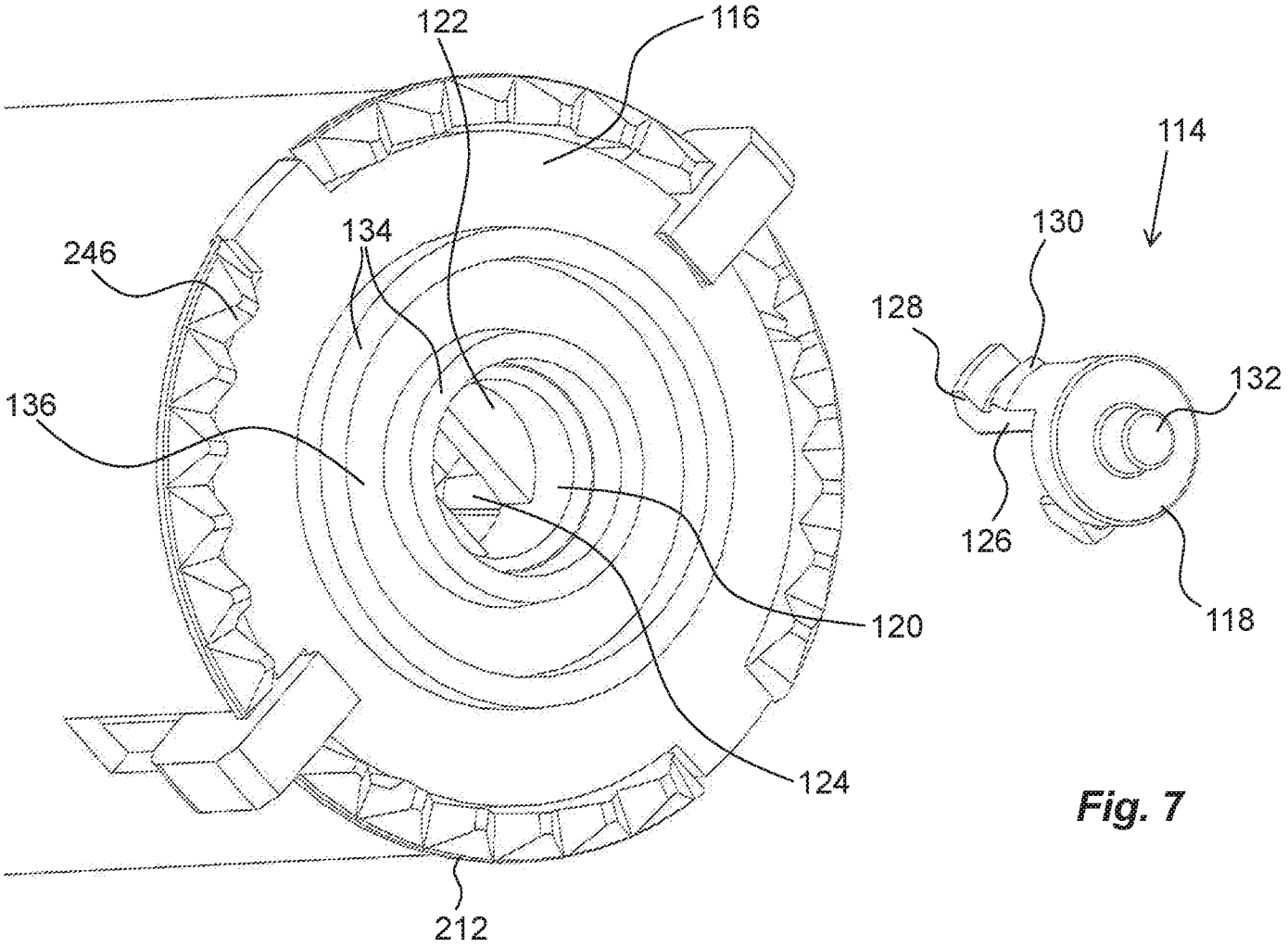
Figure 8A:
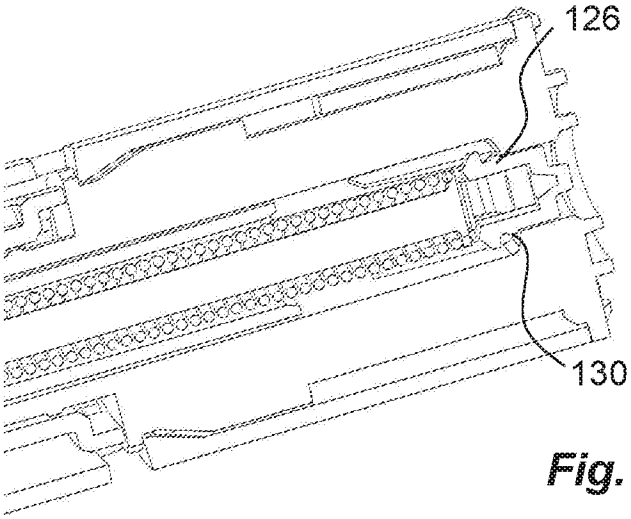
Figure 8B:
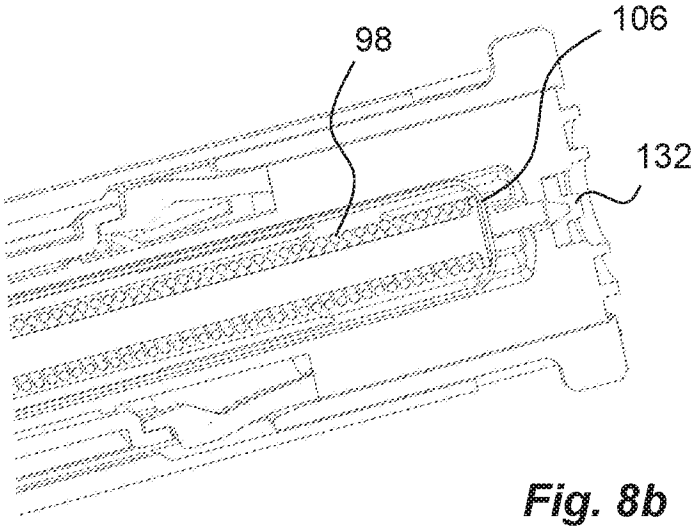

The activator 104 further comprises an activator element 114, FIGS. 6 and 7, arranged in a distal end wall 116 of the housing 10 of the medicament delivery device. In the embodiment shown the activator element 114 has a generally disk-shaped body 118 arranged to fit into a cylindrical, central passage 120 in the end wall 116. The central passage 120 is arranged with a wall section 122 having a generally rectangular opening 124. The proximally directed surface of the disk-shaped body 118 is arranged with two proximally directed tongues 126 that are somewhat flexible in the radial direction. The tongues 126 are arranged to extend through the rectangular opening 124. The free ends of the tongues 126 are arranged with outwardly directed ledges 128. Further, the outer surfaces of the tongues 126 are arranged with transversal ridges 130. In an initial position, the ridges 130 are adjacent the inner edge of the central passage 120 and the proximal ends of the tongues are in contact with the base 106 of the activator 104, as seen in FIG. 8a. The distally directed surface of the disk-shaped body 118 is arranged with a central protrusion 132. Further, the distally directed surface of the end wall 116 is arranged with a number of concentric rings 134 and grooves 136 as seen in FIG. 7.

The medicament delivery device is further arranged with a medicament delivery member shield remover 138, FIG. 1. It comprises a generally tubular grip part 140 having an end wall 142. The distally directed surface of the end wall 142 is arranged with a seat in which a generally tubular grip element 144 is placed. The grip element 144 will be coaxial with and surrounding the medicament delivery member shield 32 when the medicament delivery member shield remover 138 is attached to the proximal end of the medicament delivery device. The grip element 144 comprises a number of generally proximally directed somewhat inwardly inclined tongues 146 that are engaging the outer surface of the medicament delivery member shield 32.

Figure 9:
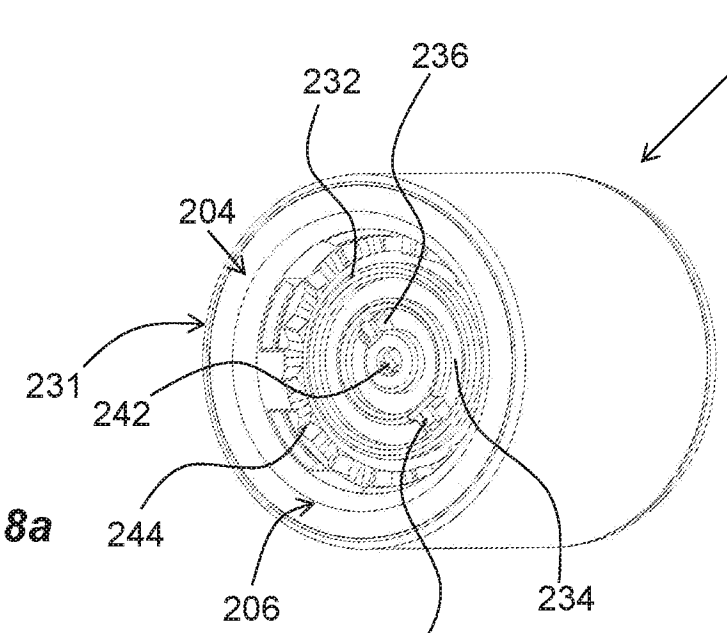
FIG. 9 shows a first embodiment of a monitoring unit according to the present disclosure.
Figure 11:
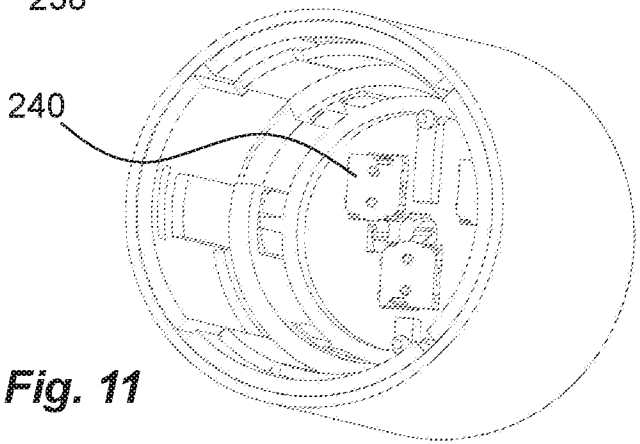
FIGS. 10-11 show detailed views of the monitoring unit of FIG. 9.

According to the present disclosure, a monitoring unit 200, FIGS. 9 and 11, is arranged to be operably connected to a medicament delivery device such as described above. The monitoring unit 200 comprises a housing 202 that could have a corresponding shape and appearance as the medicament delivery device that it is to be connected to, even though that is no prerequisite. The housing 202 has a proximally directed attachment mechanism 204 that is designed to interact with a distal end of the medicament delivery device. In the embodiment shown, the attachment mechanism 204 comprises a central passage 206 which has a shape and dimension so as to fit onto the distal end of the medicament delivery device.

Figure 10:
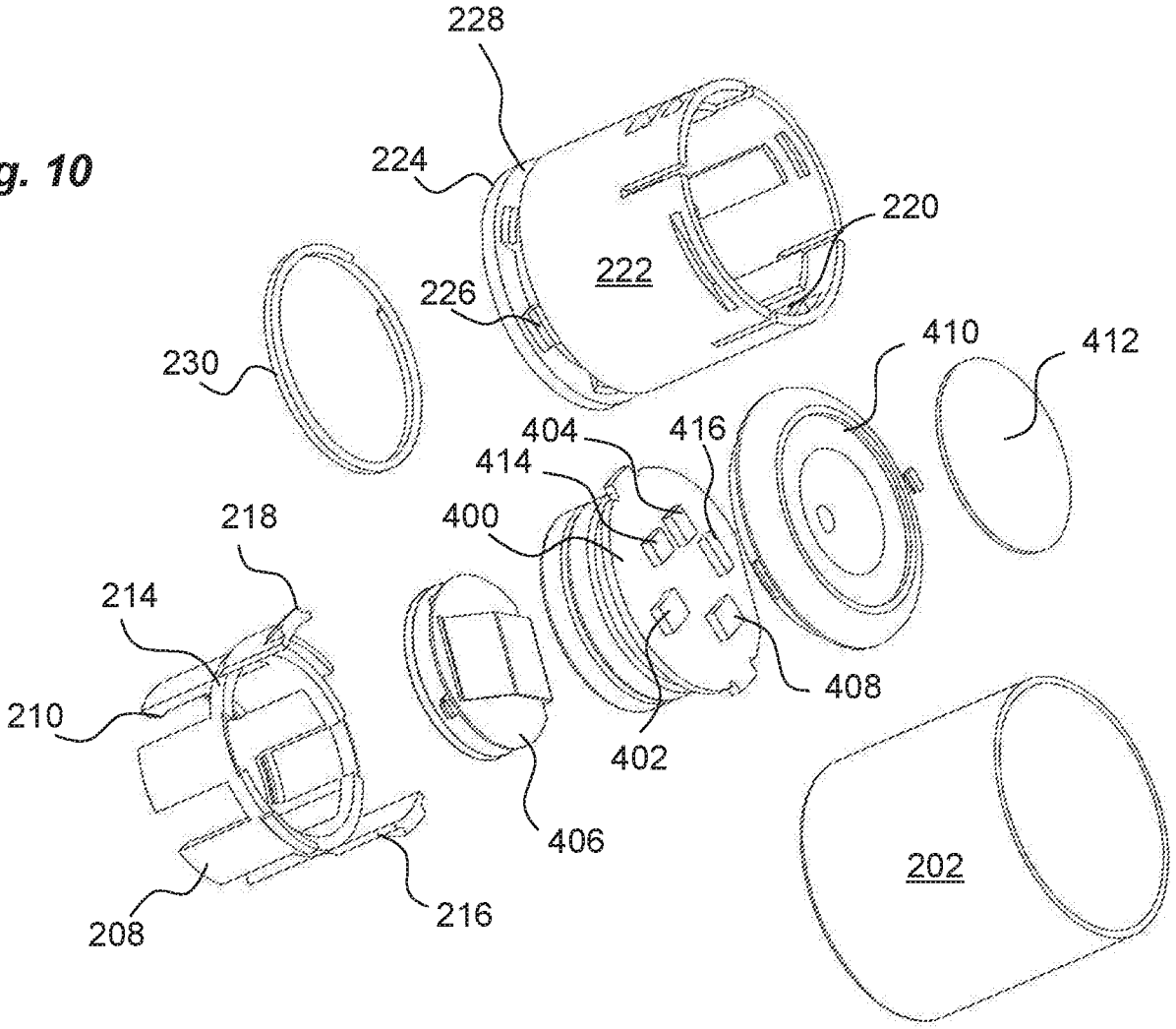

In order for the connection to be releasable, the attachment end of the monitoring unit 200 is arranged with an attachment mechanism that comprises locking elements in the form of a number of attachment tongues 208, FIG. 10, that are flexible in the generally radial direction. The free ends of the attachment tongues 208 are arranged with inwardly directed ledges 210 that are to cooperate with corresponding locking elements in the form of an annular ledge 212, FIG. 7, at the distal end of the housing of the medicament delivery device. The attachment tongues 208 are attached to a ring-shaped element 214, which ring-shaped element 214 is arranged with two oppositely positioned, distally directed, tongues 216. The free ends of the tongues 216 are arranged with outwardly directed ledges 218, which ledges are arranged to fit into recesses 220 in a tubular holding member 222. The holding member 222 is arranged with a plate-shaped contact element 224 at its proximal end, where the holding member 222 and the contact element 224 are interconnected by a number of bridges 226. The bridges 226 are placed somewhat radially inwards in relation to the holding member 222 such that an annular recess 228 is formed. Further, in the spaces between the bridges 226 the free ends of the attachment tongues 208 are placed. The attachment tongues 208 and the bridges 226 are designed and positioned such that the outer surfaces of the tongues 208 are placed somewhat radially outside the bridges 226. Further a wire spring 230 is arranged in the annular recess 228, whereby it is in contact with the outer surface of the attachment tongues 208, providing a resilient force in the outwards radial direction.

A mechanical interface 231 is arranged on the monitoring unit 200. The mechanical interface may comprise a number of rings 232 and grooves 234 on the proximally directed surface of the contact element 224 having a design that fits together with the rings 134 and grooves 136 of the end surface of the medicament delivery device, forming a contact interface. Further, the contact element is preferably arranged with a number of passages 236, in which passages 236 switches 238 are placed. The switches are operably connected to electrical switching elements 240, FIG. 11, that will enable activation of the monitoring unit as will be described. Preferably the switches 238 are arranged and designed to interact with contact surfaces on the medicament delivery device such that the switches are activated when the monitoring unit is attached to the medicament delivery device. Preferably the positions of the switches 238 of the electrical switching elements are arranged in a certain pattern that can be specific for a certain monitoring unit and wherein a certain medicament delivery device is arranged with contact surfaces that have the same design so that all switches are activated when the monitoring unit is attached to the medicament delivery device. In this manner, there is a further keying requirement that needs to be fulfilled in order to activate the monitoring unit. For example the contact surfaces are the rings and grooves wherein the switches are positioned at different distances in a radial direction as seen in FIG. 9. The advantage with having rings is that the angular position between the monitoring unit and the medicament delivery device is not important when the two are interconnected. Further, as seen in FIG. 9, since the switches 238 are placed in the grooves 234, manipulation of the switches 238 by fingers is difficult, providing increased security against improper use of the monitoring unit 200.

Further, in order to activate the monitoring unit at a certain point of operation of the medicament delivery device, such as for instance at the end of a dose delivery sequence, the monitoring unit may be provided with an activation switch 242. In the embodiment shown in FIG. 9, this activation switch 242 may be placed in a central position of the interface of the monitoring unit. The activator of the medicament delivery device is then used for activating the monitoring unit as will be described.

The interface between the medicament delivery device and the monitoring unit could further comprise mechanical patterns that are to interact with each other. For instance the proximal surface of the contact element 224 could comprise a number of teeth 244 for example around a circumference. These teeth 244 are arranged to cooperate with corresponding teeth 246 on the distal end of the medicament delivery device, wherein the number of teeth, the design of the teeth and the positions of the teeth are chosen such that a keying function is obtained. Thus, only monitoring units 200 and medicament delivery devices that have the same pattern can be inter-connected. This provides the possibility of customizing the monitoring unit 200 with the medicament delivery device such that only certain connections are possible.

Figure 12:
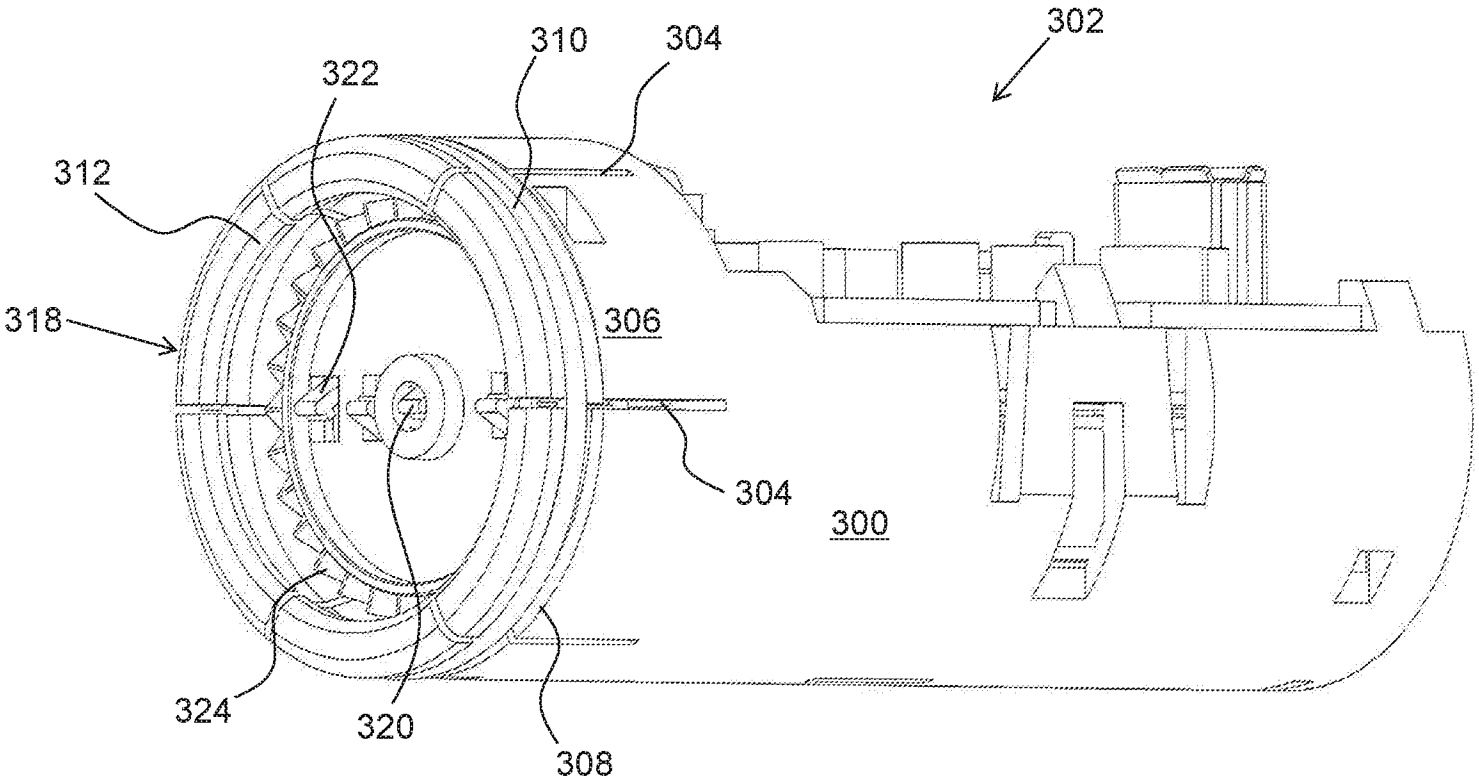
FIG. 12 shows a second embodiment of a monitoring unit according to the present disclosure.
Figure 13:
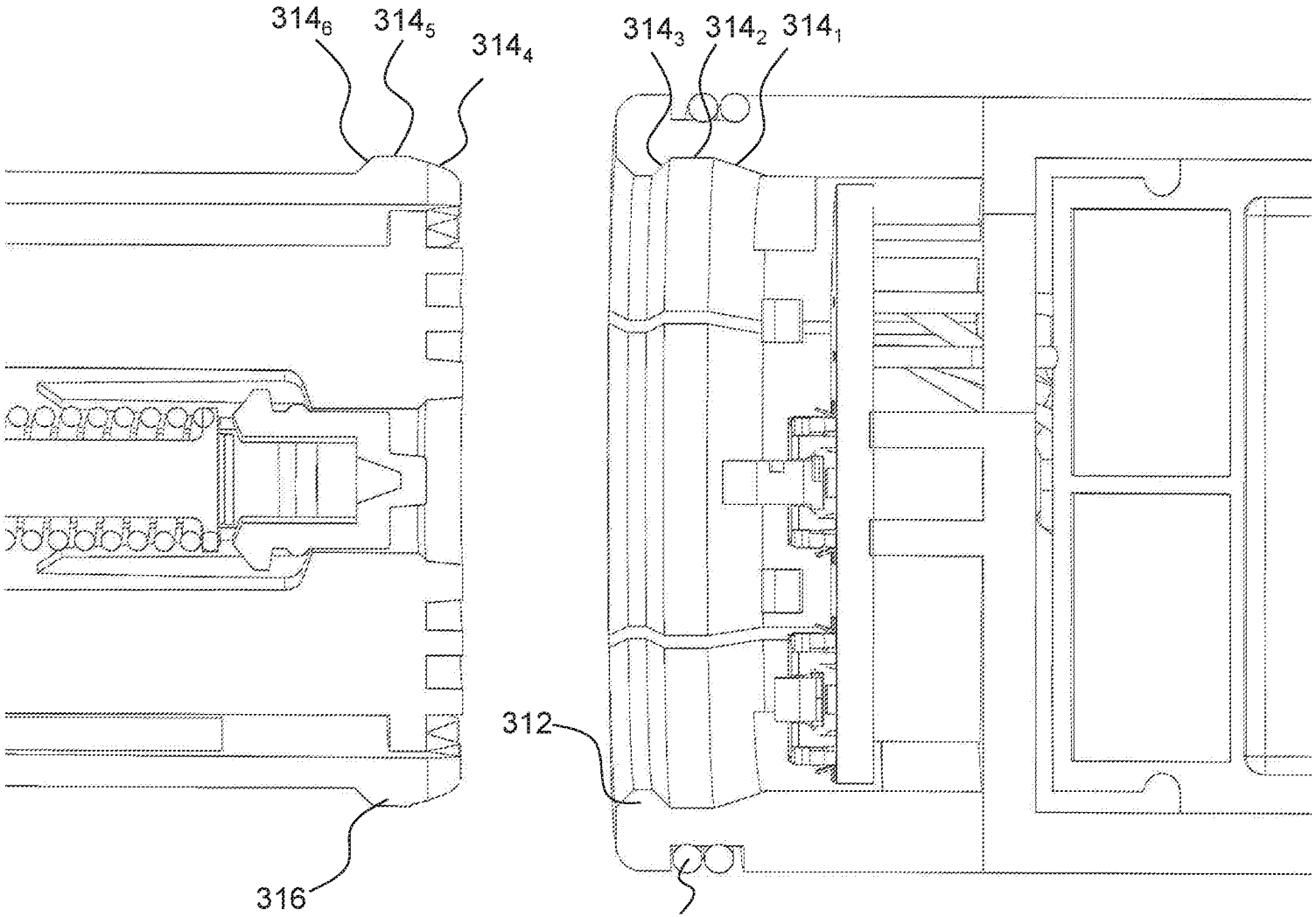
FIGS. 13-14 show detailed views of the monitoring unit of FIG. 12, FIGS. 15-18 show different functional views of the interaction between the monitoring units of FIGS. 9 and 12 and the medicament delivery device of FIG. 1, and FIGS. 19-26 show different types of monitoring and activation sensors that could be utilized in the monitoring unit.

FIG. 12 displays another connection and interface solution. Here a proximal end of a housing 300 for a monitoring unit 302 is arranged with an attachment mechanism that comprises locking elements in the form of a number of longitudinal slits 304, thereby forming a number of tongues 306 between the slits 304, which tongues 306 are flexible in the generally radial direction. Further, an annular groove 308 is arranged on the outer surface of the tongues 306. In the groove 308, a wire spring 310 is placed, which is limiting the flexing movement of the tongues 306. The tongues 306 are further arranged with inwardly directed ledges 312. The inner surfaces of the free ends of the tongues 306 and the inwardly directed ledges 312 have a cross-sectional view that comprises a first proximally directed inclined surface $\mathbf{314}_1$, FIG. 13, a second generally flat surface $\mathbf{314}_2$ that is parallel with the tongue 306, and a third distally directed inclined surface $\mathbf{314}_3$.

Figure 14:
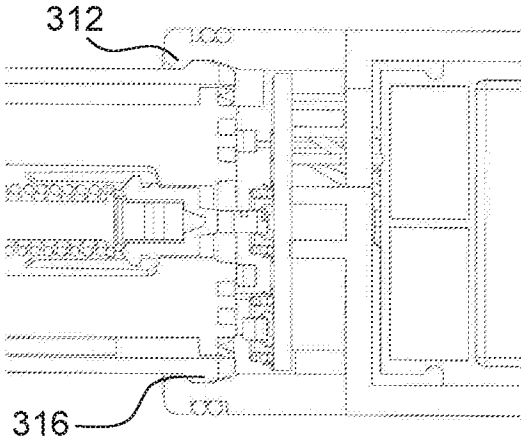

The interface of the medicament delivery device is arranged with corresponding locking elements in the form of an annular ledge 316. The ledge 316 is arranged with a fourth distally inclined surface $\mathbf{314}_4$ that preferably has a small inclination, in the region of 5-15 degrees as seen in the longitudinal direction intended to interact with the surface $\mathbf{314}_1$. A fifth generally flat surface $\mathbf{314}_5$, parallel with the longitudinal direction is arranged connected to the fourth distal inclined surface $\mathbf{314}_4$. The fifth flat surface $\mathbf{314}_5$ is arranged to cooperate and be in contact with the second flat surface $\mathbf{314}_2$ of the monitoring unit as seen in FIG. 14. The flat fifth surface $\mathbf{314}_5$ transcends into a sixth proximally directed, inclined surface $\mathbf{314}_6$. The sixth surface $\mathbf{314}_6$ has a steeper inclination which could be in the region of 30-60 degrees. The sixth surface $\mathbf{314}_6$ is arranged to be in contact with and cooperate with the third surface $\mathbf{314}_3$ of the monitoring unit, see FIG. 14.

The inclination of the fourth surface $\mathbf{314}_4$ is chosen such that the force required for attaching the monitoring unit 302 to the medicament delivery device is rather small, i.e. the tongues may flex rather easily when they are contacting the ledge of the medicament delivery device. Further, the inclinations of the third surface $\mathbf{314}_3$ and the sixth surface $\mathbf{314}_6$ are chosen such that there is a rather strong holding force when the monitoring unit is attached to the medicament delivery device. Further, the engagement length of the contact surfaces of the monitoring unit and the medicament delivery device is chosen rather short. This choice is made to facilitate the attachment of the monitoring unit as well as to increase the bending force required for releasing the connection. A mechanical interface 318 of the second embodiment is arranged with a centrally placed activation switch 320 as well as three switches 322 where the activation could be made in different combinations in order to provide different information when the monitoring unit is activated. For instance different combinations might indicate different drug strengths of the medicament container used. The mechanical interface 318 further comprises annularly arranged teeth 324 that are arranged to interact with annularly arranged teeth with the same mechanical design on a distal end of a medicament delivery device as described above.

Even though the mechanical interface has been described with annularly arranged teeth and ring-shaped protrusions and ring-shaped grooves, the skilled person can easily design other mechanical configurations that provide a unique keying function.

The device is intended to function as follows. When the medicament delivery device is delivered to a user, a medicament container 18 with an attached medicament delivery member shield 32 has been placed in the medicament container holder 20 and a medicament delivery member shield remover 138 has been attached to the proximal end of the medicament delivery device. The drive spring 98 has been tensioned by pushing the plunger rod 94 distally relative to the actuator 56 such that the inwardly directed protrusions 90 of the arms 86 of the actuator 56 engage the recesses 92 of the plunger rod 94, thereby holding the spring-biased plunger rod 94.

Figure 15:
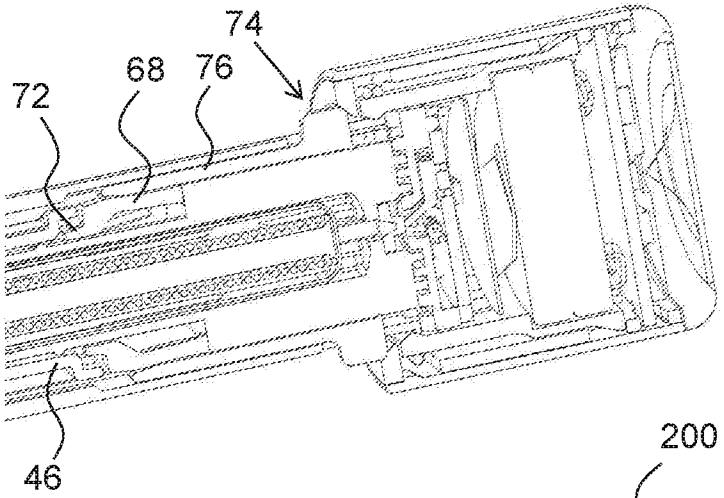

When a medicament delivery device is to be used, a monitoring unit 200, 302 has to be attached. The monitoring unit is thereby pushed onto the distal end of the medicament delivery device, whereby a proximal surface of the monitoring unit comes in contact with a distal surface of the protrusions 82 of the release element 74. Further pushing of the monitoring unit 200, 302 in relation to the medicament delivery device will cause the release element 74 with its plate-like members 76 to be moved in the proximal direction. The proximal ends of the plate-like members 76 then act on the tongue-shaped sections 68 such that the tongue-shaped sections 68 are moved radially inwards whereby the ledges 72 are moved out of engagement with the space 55 of the rotator 46, FIG. 15, whereby the rotator 46 is free to rotate as will be described. When now the monitoring unit is attached to the medicament delivery device, the interfaces of the two are keyed to each other if the proper monitoring unit is used to the intended medicament delivery device. Some of the switches are then activated by the interface, making the monitoring unit ready for activation and for performing functions as will be described below.

When a dose of medicament is to be delivered, the medicament delivery member shield remover 138 is removed from the proximal end of the medicament delivery device by pulling it in the proximal direction. Because of the engagement of the tongues 146 with the medicament delivery member shield 32, the medicament delivery member shield 32 will also be pulled in the proximal direction, removed from the medicament delivery member 30. The proximal end of the medicament delivery device is then pressed against a dose delivery site. This causes the medicament delivery member guard 36 to move inside and relative the housing 10. This in turn causes the protrusions 44 of the medicament delivery member guard 36 to move along the guide ridges 50 of the rotator 38 such that the protrusions will come in contact with the inclined guide ridge $\mathbf{50}_i$, which will cause the rotator 46 to turn around the longitudinal axis L of the device i.e. to rotate.

Thus, as described above, if the monitoring unit 200, 302 has not been previously attached, the rotator will be prevented from rotating and, consequently, it will be impossible to use the device.

The turning/rotation of the rotator 46 will cause the outwardly directed protrusions 88 of the actuator 56 to be moved out of contact with inner surfaces of the rotator 46. The arms 86 of the actuator 56 are now free to flex outwardly, whereby the inwardly directed protrusions 90 of the arms 86 are moved out of contact with the recesses 92 of the plunger rod 94.

Figure 16:
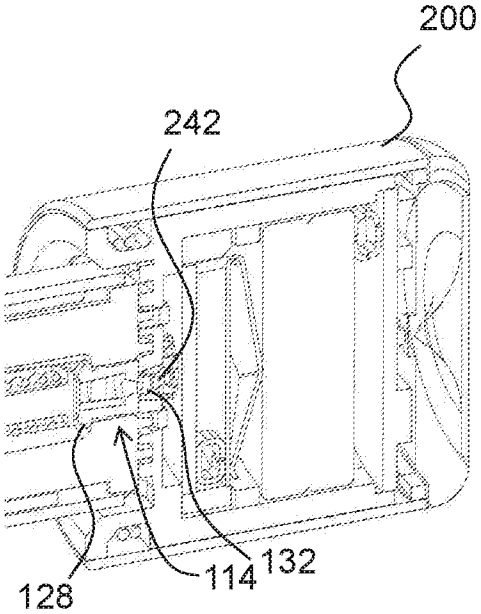

The plunger rod 94 is now free to move in the proximal direction due to the force of the drive spring 98, wherein the proximal end of the plunger rod 94 acts on, and moves, the stopper 28 inside the medicament container 18 in the proximal direction such that a dose of medicament is expelled through the medicament delivery member 30, FIG. 16.

Figure 17A:
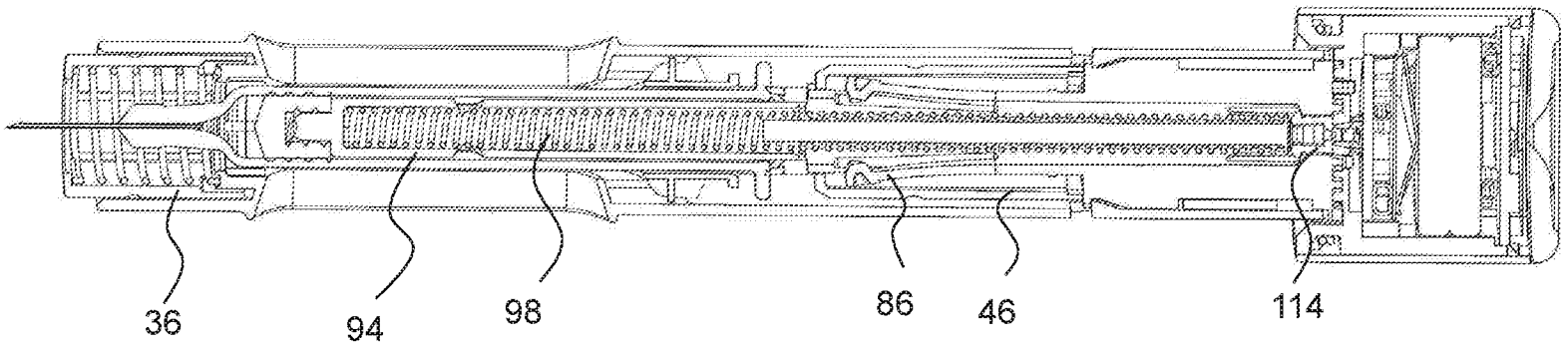
Figure 17B:
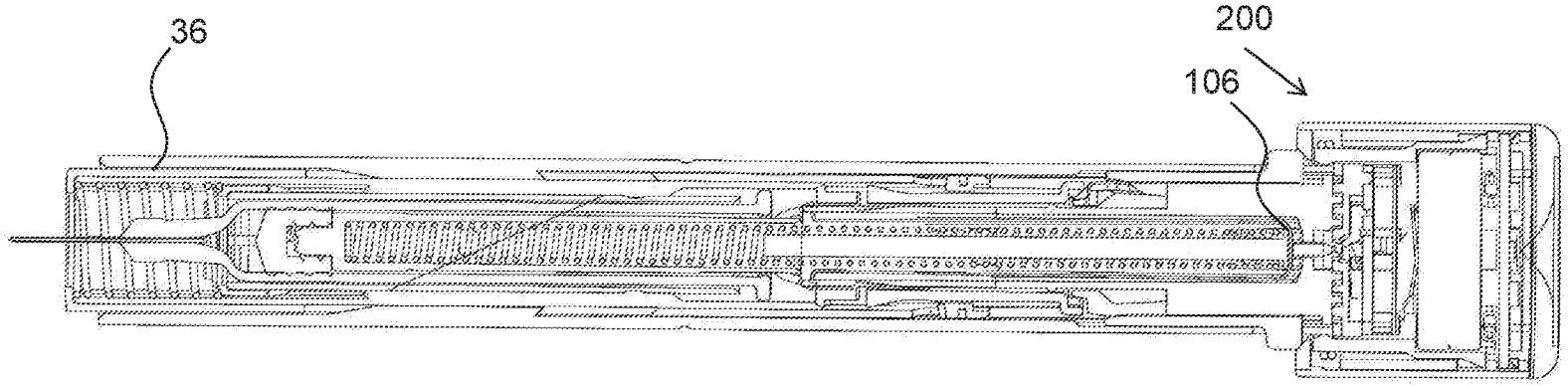

When the stopper 28 has been moved by the plunger rod 94 to almost the proximal end inside the medicament container 18, the plunger rod 94 is moved out of contact with the arms 108 of the activator 104. The arms 108 of the activator 104 are thus free to flex inwards such that the ledges 110 are moved out of contact with the surfaces 112 of the actuator 56, and due to the force of the drive spring 98 in contact with and acting on the base 106 of the activator 104, the activator 104 will be moved in the distal direction. Because of the contact with the activator element 114, the activator element 114 will also be moved distally in the central passage 120 such that the central protrusion 132 will extend out of the central passage 120 and affect the activation switch 242 of the monitoring unit, FIG. 17, whereby the monitoring unit 200 is activated as will be described below. The movement of the activator element 114 is stopped when the outwardly directed ledges 128 hit a proximally directed surface of the end wall 116 of the medicament delivery device. This sudden stop will also provide an audible and tactile signal that the dose delivery sequence is completed and that it is safe to remove the medicament delivery device.

Figure 18A:
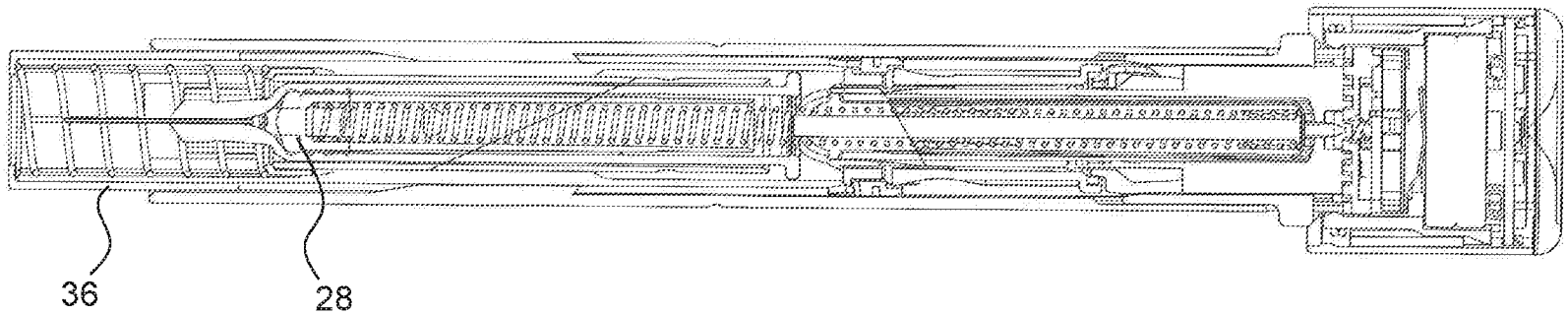
Figure 18B:
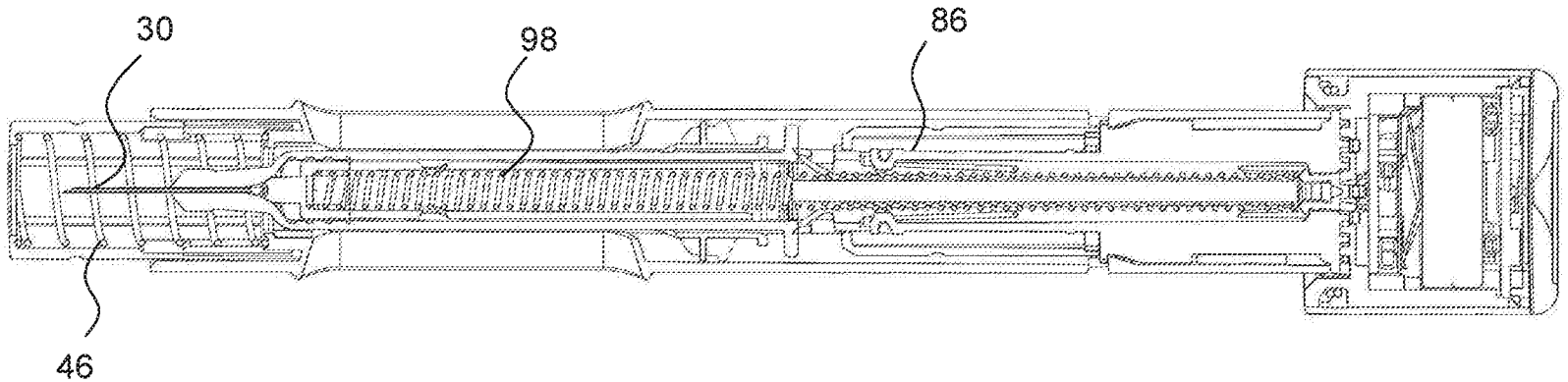

When the dose has been delivered the medicament delivery device is removed from the site. This in turn will cause the medicament delivery member guard 36 to be moved in the proximal direction by the medicament delivery member shield spring 42, to extend through the proximal end of the medicament delivery device and to cover the medicament delivery member 30. Since the rotator 46 has been rotated, the protrusions 44 of the medicament delivery member guard 36 will slide over the wedge-shaped protrusions 54 of the tongues 52 of the rotator 46 and be placed proximally thereof, thereby locking the medicament delivery member guard 36 in the extended, covering position, FIG. 18. The device can now be discarded in a safe manner.

The monitoring unit 200, 302 is arranged with a number of functions and features that may be activated when the activation switch 242 is operated as described above. One basic feature is a monitoring circuit that comprises an electronic circuit 400 comprising a processor 402, FIG. 10, capable of processing data program code for performing different tasks. The data program code is preferably stored in appropriate memory elements 404, in which also retrieved data may be stored, as will be described. The electronic circuit 400 is further arranged with some power supply 406 such as button cells, photovoltaic panels, etc. Further, the above mentioned switching elements 240, 242 are electronically connected to the electronic circuit 400. In this respect it might be that all switches need to be operated at the same time in order for the monitoring unit to be activated. The electronics circuit may further be arranged with a user communication circuit 408 that is arranged and programmed to communicate with a user. The user communication circuit 408 may comprise display elements that can communicate visually, e.g. by text stored in the electronics module that is displayed on a suitable display 410 on the monitoring unit. The display may be protected by a suitable transparent cover or glass 411. In addition to, or instead, the user communication circuit may comprise audio elements 412 that can communicate audibly, e.g. by a recorded message stored in the electronics module that is played in an appropriate loudspeaker of the electronics module or of the device as such.

A further development of the activation function is to provide the monitoring unit 200, 302 with at least one communication circuit 414. The communication technologies that the communication circuit 414 may utilize may comprise near range communication technology such as RFID, NFC or the like, as well as Bluetooth, Ant, ZigBee, just to mention a few. This type of wireless communication technology may also be used to activate the monitoring unit. The communication circuit may be used for monitoring the usage of the medicament delivery device such that information is transmitted from the medicament delivery device to the monitoring unit.

According to a possible feature, if the monitoring unit 200, 302 is provided with communication circuits, then monitored data obtained by the monitoring unit may be transferred to external storage sources and/or external devices. If for instance NFC technology is used, then a mobile NFC-enabled device may derive the monitored data from the usage management module. The same functionality may also be provided when using Bluetooth communication technologies.

The mobile device may then either be capable of processing the data, such as e.g. calculating the time and date of an occurrence of the medicament delivery device, or may in turn transmit the monitored data to external databases via the communication technologies of the mobile device, such as cellular radio communication networks, e.g. GSM, 3G, 4G, etc. and/or wireless local area networks, which networks can provide access to the internet and thus to a large number of external data storage sources, data handling centres, etc.

Regarding communication technologies, it is of course possible to incorporate the above mentioned communication technologies in the monitoring unit 200, 302 as such. Then the monitoring unit may communicate directly with external data storage sources, data handling centres etc. via the communication networks. The monitored data may preferably be accessible to a physician or the like skilled person that is responsible for the treatment of the user of the medicament delivery device and who might have put together a treatment scheme. This retrieved monitored data may then be evaluated to derive information such as adherence, and the lack of which may lead to measures from the physician.

The electronic circuit 400 may further be arranged with a positioning function whereby the geographical position of the user may be obtained and used for different purposes. In this respect, the positioning may be obtained by different functions. Either the electronics circuit is provided with a GPS-module, whereby the actual position of the user when the dose is delivered is recorded by GPS coordinates. Another possibility is to use the GSM-function for locating the position. The GPS-function and the GSM-function may further be combined with a WIFI location function for improved indoors location.

Regarding the activation of the monitoring unit, the electronic circuit could preferably be arranged with a suitable switch-off functionality, such as a timer function that will switch off the power to the circuitry after a certain period of time, for instance after completed medicament delivery operation. This will prolong the life of the power source in that it is not active when no action is taking place. Further, the electronic circuit may be arranged with a delay function that for example delays the sending of certain information. This may be used if the monitoring unit is activated during a dose delivery sequence but not at the end. The signal that the dose has been delivered can then be delayed so that it is ascertained that the whole dose has been delivered. The signal may for example be an audible signal from the monitoring unit to be heard by the user. With this delaying function, the point of activation of the monitoring unit is not so critical.

Since the monitoring unit is detachable from the medicament delivery device, it may be used together with disposable medicament delivery devices as well as re-usable medicament delivery devices and since it may be used many times with many devices and/or many dose delivery operations, it does not increase the total cost of a medicament treatment scheme in any major way.

Further, even though the activation of the monitoring unit has been described in relation to an end of dose operation, it is to be understood that the monitoring unit may be activated by a number of different features, functions and operations such as e.g. removal of protective caps, penetration of an injection needle, start and/or end of a dose delivery sequence, shielding of an injection needle after withdrawal. The skilled person working with design of medicament delivery devices has no difficulties in identifying suitable occurrences during the operation of a medicament delivery device when an activation feature may be added.

Figure 19:
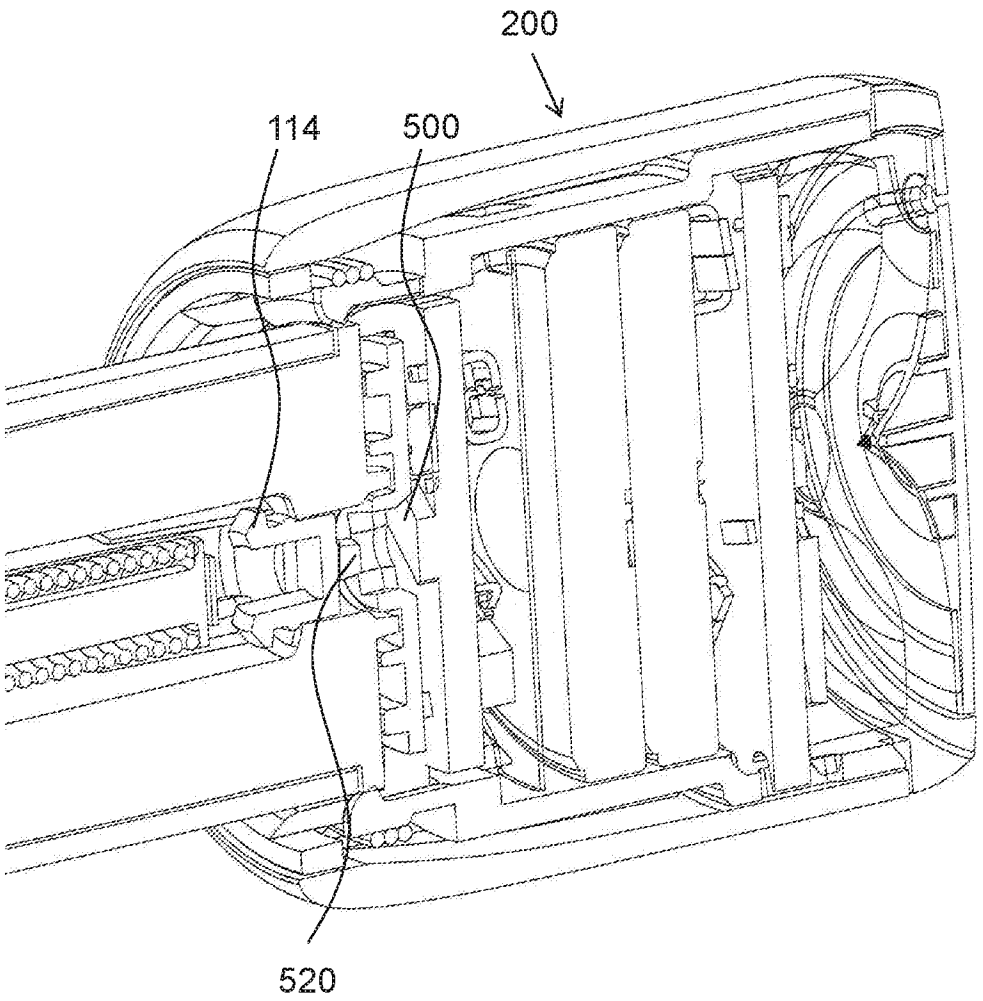

The present disclosure may activate the monitoring unit in a number of ways other than pure mechanical. FIGS. 19-26 show a number of different feasible solutions where the end of dose is signaled and the monitoring unit is activated. FIG. 19 shows a shock or vibration sensor 500 positioned in the vicinity of the activator element 114. For instance when the monitoring unit 200 is connected to the medicament delivery device, the switches 238 of the monitoring unit 200 will be triggered as described above and will wake up the electronics circuit with the processor that in turn powers and monitors the shock sensor 500. The shock or vibration sensor 500 may be capable of sensing the vibration that is generated when an injection is started, which is recorded by the sensor 500 via the housing of the medicament delivery device and the connection with the monitoring unit 200. Then at the end of the injection the end click that is generated by the drive spring as described above, will be registered by the shock sensor 500. Vibration may be created by the activator element hitting the shock sensor directly, or the activator element hitting the housing of the monitoring unit or the activator hitting the end wall.

Figure 20:
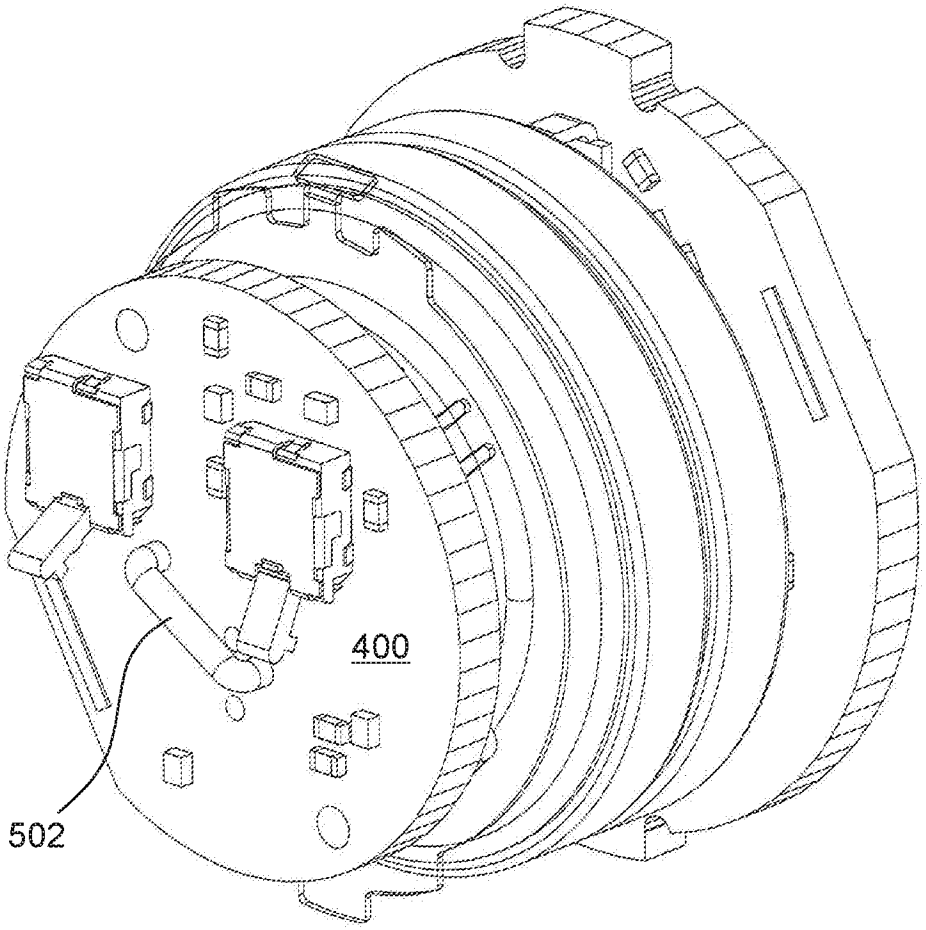
Figure 21:
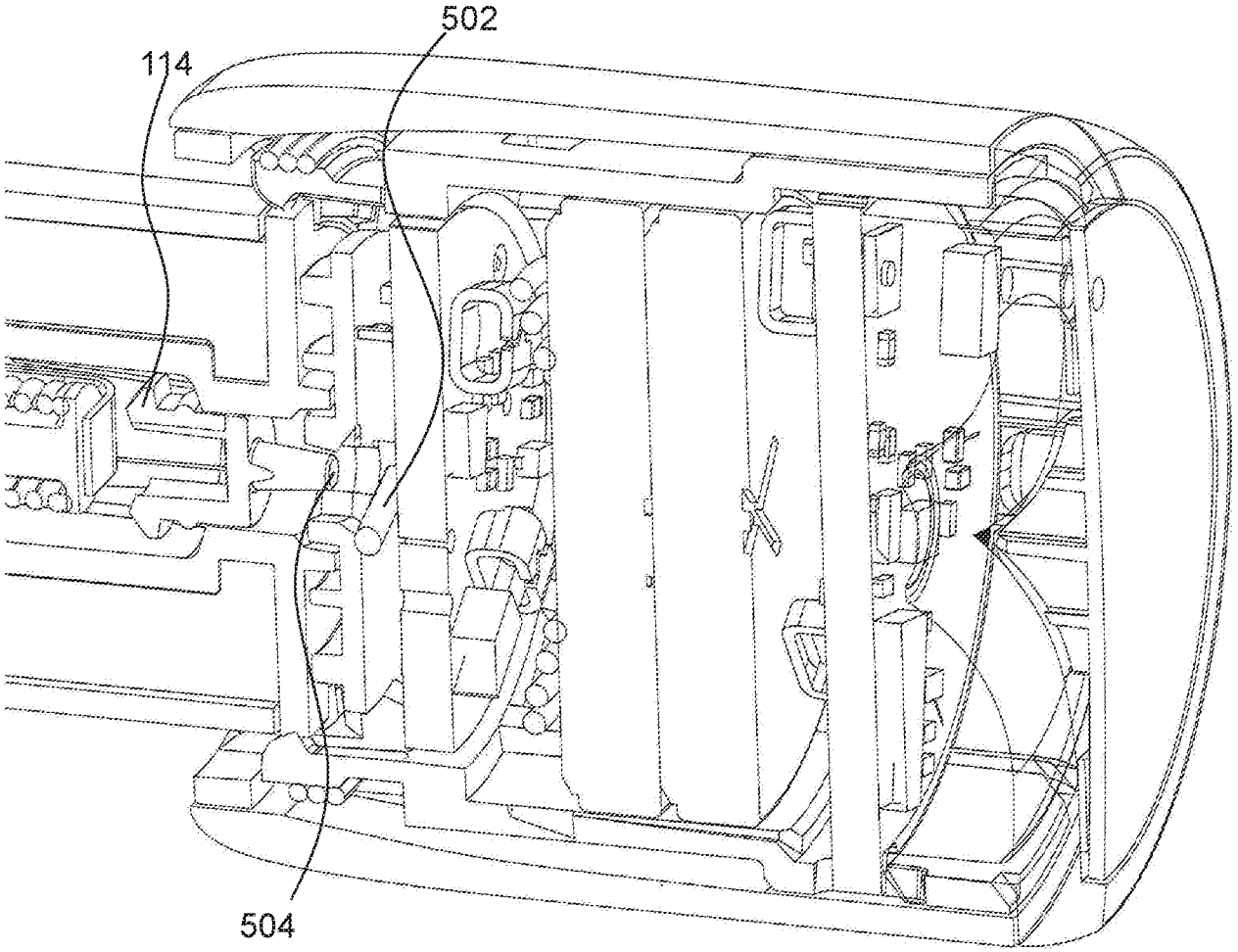

FIGS. 20 and 21 show an alternative solution in which a reed switch 502 may be utilized. A reed switch 502 is connected to the printed circuit board 400 in the vicinity of the activator element 500. The activator element 114 is then arranged with a magnet 504, FIG. 21. Before the end of injection, the activator element 114 with its magnet 504 is placed such that there is a distance to the reed switch 502 such that the reed switch is in its off state. At the end of the injection, the activator element 114 is moved in the distal direction as described above, wherein its magnet 504 is moved closer to the reed switch, whereby the reed switch is switched to its on state.

Figure 22:
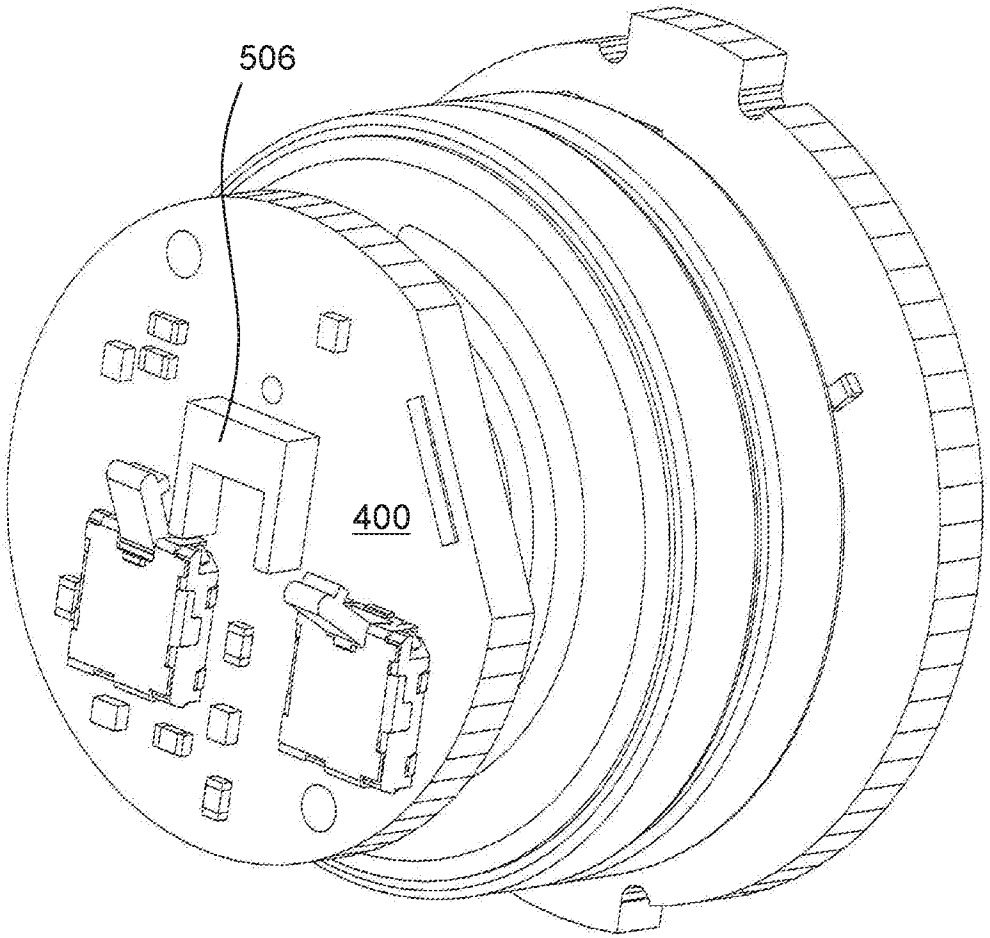
Figure 23:
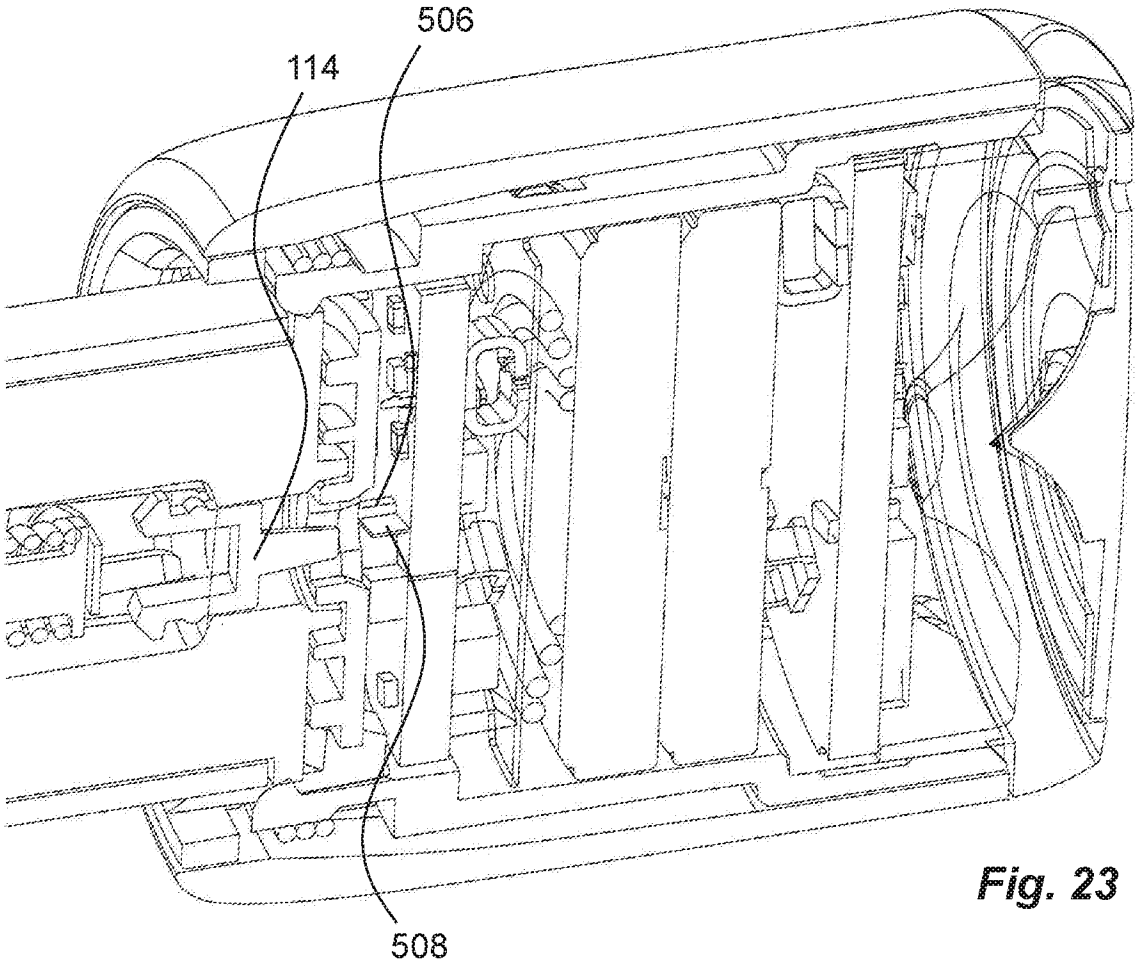

Another feasible solution is shown in FIGS. 22 and 23. Here an opto or photo interrupter sensor 506 is used. It has a general U-shape with a light source on one of the arms and a light detector on the other arm facing towards each other. The light source may be a LED and the light detector a photo diode. When the monitoring unit is activated upon connection to the medicament delivery device, the light source will emit a light beam 508 that is detected by the light detector. The photo interrupter sensor 506 may be placed in the vicinity of the activator element 114 such that a distal end of the activator element 114 is moved into the U-shape of the photo interrupter sensor 506 at the end of injection, thereby breaking or interrupting the beam of light 508 between the light source and the light detector. This interruption is sensed by the electronics, providing an indication of the end of injection.

Figure 24:
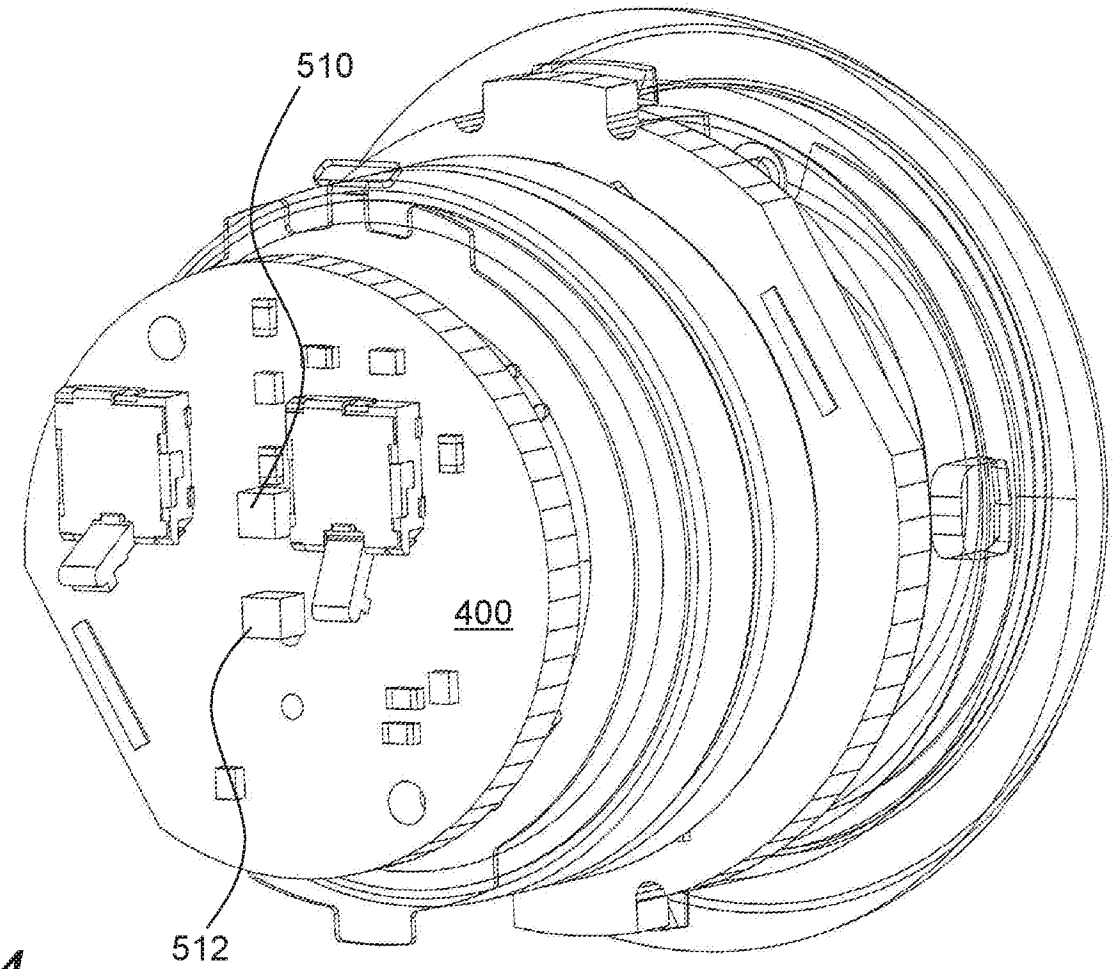

Regarding the use of light, a light source 510 such as a LED may be positioned adjacent the distal end of the activator element, FIG. 24. Further an optical sensor 512 is arranged such that light that is emitted from the light source 510 and reflected on a distally directed surface of the activator element is 114 detected by the optical sensor 512. When the activator element 114 is moved in the distal direction by the activator at the end of an injection sequence, the decreased distance between the activator element 114 and the optical sensor 512 will be detected thereby activating the monitoring unit 200.

Figure 25:
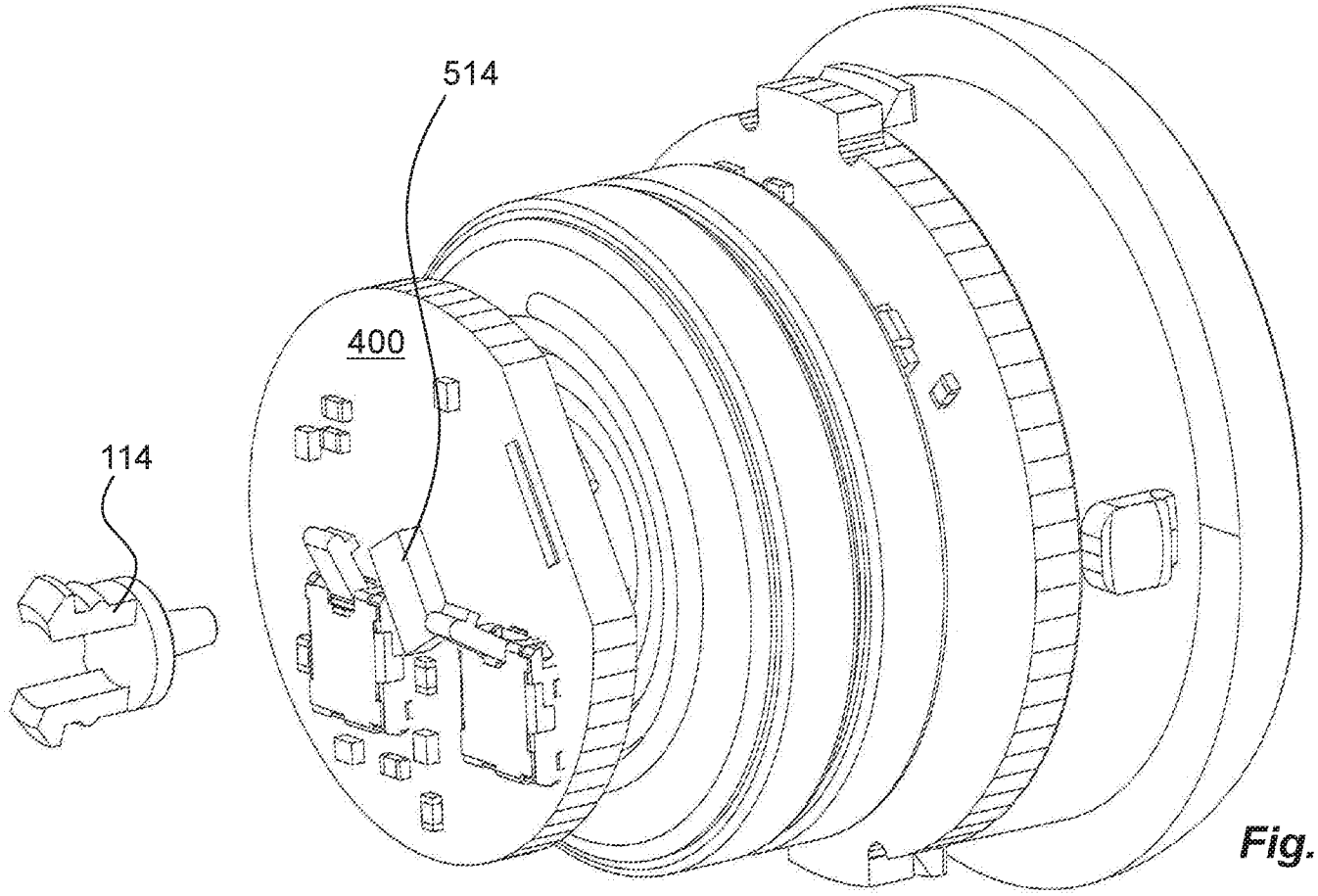
Figure 26C:
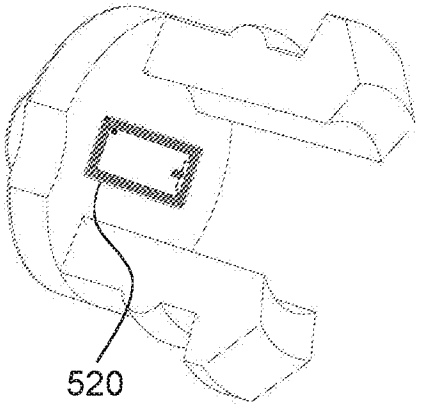
Figure 26B:
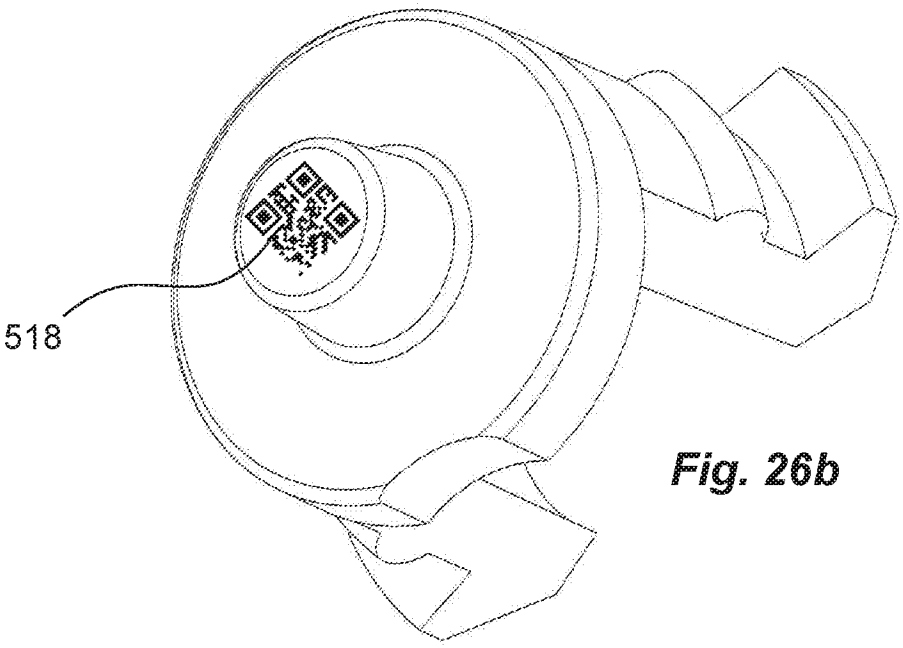
Figure 26A:
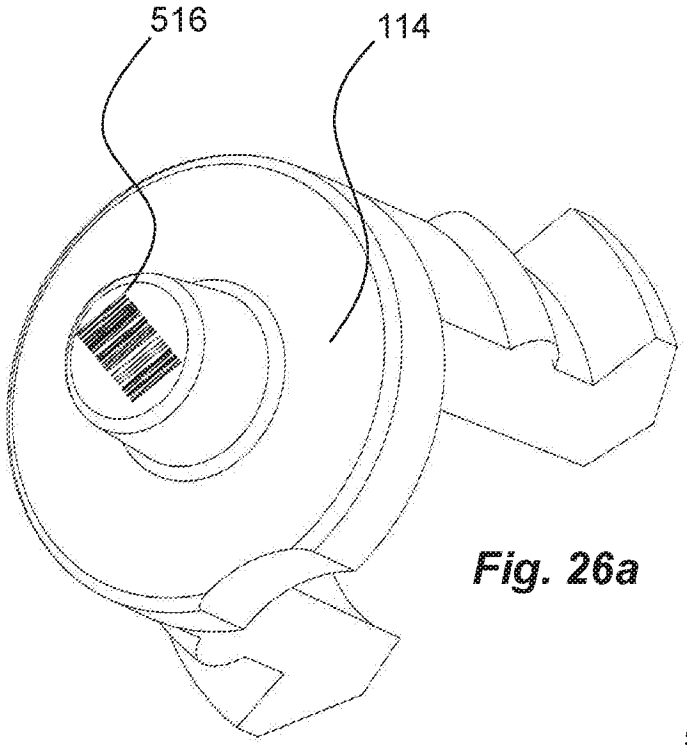

A number of other types of sensors 514 may be used for detecting the movement of the activator element as seen in FIG. 25. One type of sensor 514 may be a capacitive proximity sensor. This sensor 514 is also placed adjacent the distal end of the activator element such that the proximity sensor can detect the movement of the activator element 114 when it moves at the end of the injection.

A further type of sensor 514 is an ultrasonic sensor which may be positioned in the vicinity of the activator element 114. The ultrasonic sensor is capable of detecting the displacement of the activator element 114 during the end of injection sequence.

Yet a further type of sensor is a hall effect sensor that is positioned adjacent the activator element 114, wherein the activator element is arranged with a magnet 504, such that the activator element when moving in the distal direction enters the area of the hall effect sensor, whereby the hall effect sensor detects the magnet of the activator element, thereby activating the monitoring unit 200.

The activator element may further be used to transmit data from the medicament delivery device to the monitoring unit. Data that could be transmitted is the type of medicament and/or the medicament volume. In order to do this the activator element is arranged with some sort of information that can be derived by the monitoring unit. In that respect the activator element may be arranged with different colours, where a certain colour represents certain information. The monitoring unit is then arranged with a sensor 514 that is capable of detecting certain colours, such as an RGB sensor and which is placed so that it can detect the colour on the activator element 114. For instance, the colour red may be connected to information stored in the monitoring unit of a specific dose size. When the monitoring unit now is connected to the medicament delivery device, the RGB sensor may detect the red colour and activate the monitoring unit 200 to indicate that it is connected to a medicament delivery device having a medicament container of a specific dose size.

Instead of colour, other types of information carriers may be used, such as a bar code containing certain specific information. With this solution, the sensor 514 is a bar code reader that is positioned adjacent the activator element 114. The activator element is arranged with a bar code 516, FIG. 26a, on a distally directed surface thereof such that is readable by the bar code reader. As an alternative to the bar code, a QR-code 518, FIG. 26b, could be utilized at the distal end of the activator element 114, where the sensor 514 is a QR-code reader 530. Both the bar code 516 and the QR-code 518 could contain more information that could be obtained by the monitoring unit 200. Another solution could comprise an RFID chip 520, FIG. 26c, attached to or molded into the activator element. The sensor 514 of the monitoring unit may then be an RFID reader placed in the vicinity of the activator element, wherein the RFID reader is capable of obtaining data stored in the RFID chip 520. The RFID chip 520 could contain different information that the monitoring unit could derive.

It is to be understood that the embodiments described above and shown in the drawings are to be regarded only as non-limiting examples of the disclosure and that it may be modified in many ways within the scope of the patent claims.

The invention claimed is:

1. A monitoring unit for a medicament delivery device, the monitoring unit comprises;

a housing comprising a longitudinal axis, a distal end and a proximal end;

a monitoring circuit arranged in said housing that can detect and monitor functions of the medicament delivery device;

an attachment mechanism comprising a ring shaped element having proximally directed releasable locking elements that are configured to flex radially to releasably attach to a terminal distal end of an outer housing of the medicament delivery device such that when the monitoring unit is releasably attached to the medicament delivery device the housing of the monitoring unit extends distally and outwardly along the longitudinal axis from the outer housing of the medical delivery device;

a mechanical interface arranged to interact with a mating mechanical interface arranged on a medicament delivery device; and an activation switch arranged to activate said monitoring circuit, *wherein the activation switch is configured to activate the monitoring circuit in response to at least one of a removal of a protective cap, penetration of an injection needle, a start of a dose delivery sequence, an end of a dose delivery sequence, and a shielding of an injection needle*.

2. [The] *An assembly including the medicament delivery device and the* monitoring unit according to claim [16] *1*, wherein said medicament delivery device is arranged with an activator element operably connected to a drive element of said medicament delivery device, wherein said drive element will force said activator element in a distal direction during dose delivery, acting on said activation switch.

3. The [monitoring unit] *assembly* according to claim 2, wherein said activation switch is a reed switch or hall switch and wherein said activator element is arranged with a magnet arranged to be detected by said reed switch or said hall switch when said medicament delivery device is operated.

4. The [monitoring unit] *assembly* according to claim 2, wherein said activation switch is a capacitive proximity sensor or an ultrasonic sensor positioned such in relation to said activator element that movement of said activator element during operation of said medicament delivery device is detected.

5. The [monitoring unit] *assembly* according to claim 2, wherein said activator [unit] *element* comprises further information that can be derived from said activation switch.

6. The [monitoring unit] *assembly* according to claim 5, wherein said activation switch comprises an RGB colour sensor and wherein said activator element is provided with certain specific colours, where a specific colour is associated with certain information regarding the drug to be delivered.

7. The [monitoring unit] *assembly* according to claim 2, wherein said activation switch is a bar code reader or a QR reader and wherein said activator element is arranged with a bar code or a QR code containing information regarding the drug to be delivered.

8. The [monitoring unit] *assembly* according to claim 2, wherein said activation switch is an RFID/NFC reader and wherein said activator element is arranged with an RFID/NFC tag containing information regarding the drug to be delivered.

9. The [monitoring unit] *assembly* according to claim [8] *2*, [wherein said] *further including a* communication circuit [is] operably arranged to receive data from external data providing sources.

10. The monitoring unit according to claim 1, wherein said activation switch comprises at least one electrical switch operably arranged to activate said monitoring circuit.

11. The monitoring unit according to claim 1, wherein said activation switch is a vibration sensor arranged to detect vibrations generated when said medicament delivery device is operated.

12. The monitoring unit according to claim 1, wherein said activation switch is an opto switch arranged such that a light beam is broken when said medicament delivery device is operated.

13. The monitoring unit according to claim 1, further comprising a communication circuit operably arranged to transmit data to external data handling sources.

14. The monitoring unit according to claim 1, further comprising a user communication circuit operably arranged to communicate data with a user.

15. The monitoring unit according to claim 1, wherein said attachment mechanism comprises a number of flexible locking elements arranged to interact with mating locking elements on the medicament delivery device.

16. A monitoring unit for a medicament delivery device, the monitoring unit comprises;

a housing comprising a longitudinal axis, a distal end and a proximal end;

a monitoring circuit arranged in said housing that can detect and monitor functions of the medicament delivery device;

an attachment mechanism arranged within the proximal end of the housing, where the attachment mechanism comprises a ring-shaped element having proximally directed releasable locking elements that are configured to releasably attach to a terminal distal end of an outer housing of the medicament delivery device such that when the monitoring unit is releasably attached to the medicament delivery device the housing of the monitoring unit extends distally from the outer housing of the medical delivery device;

a tubular holding member positioned within the housing and having a plate-shaped contact member comprising a proximally directed surface that is traverse to the longitudinal axis;

a releasable mechanical interface arranged on the proximally directed surface of the contact member that is configured to releasably interact with a mating mechanical interface arranged on the terminal distal end of the outer housing of the medicament delivery device; and an activation switch arranged to activate said monitoring circuit, *wherein the activation switch is configured to activate the monitoring circuit in response to at least one of a removal of a protective cap, penetration of an injection needle, a start of a dose delivery sequence, and end of a dose delivery sequence, and a shielding of an injection needle*.

17. The monitoring unit according to claim 16, wherein the mechanical interface comprises a ring and a groove.

18. The monitoring unit according to claim 16, wherein the activation switch detects vibrations in the medicament delivery device.

19. The monitoring unit according to claim 16, further comprising a communication circuit operably arranged to receive and transmit data to external data handling sources.

20. The monitoring unit according to claim 16, wherein the attachment mechanism further comprises distally projecting tongues.

*21. An assembly comprising:*

*a medicament delivery device including an activator element configured to be displaced in a distal direction from an initial position to an activation position in response to a movement of a drive element; and*

*a monitoring unit for connection to a distal end of the medicament delivery device, the monitoring unit comprising:*

*a housing comprising a longitudinal axis, a proximal end, and a distal end;*

*a monitoring circuit arranged within the housing that detects and monitors functions of the medicament delivery device;*

*an attachment mechanism positioned at the proximal end of the housing comprising a ring shaped connector having a proximally directed and radially flexible releasable locking tongue, where the releasable locking tongue releasably connects with the distal end of the medicament delivery device such that the monitoring unit extends distally and outwardly along the longitudinal axis away from the distal end of the medical delivery device; and*

*an activation switch electrically connected to the monitoring circuit, where, when the activator element is in the activation position, the activator element acts on the activation switch to activate said monitoring circuit.*

*22. The assembly of claim 21, wherein a contact between the activator element and the activation switch is initiated as the activator element is displaced from the initial position to the activation position.*

*23. The assembly of claim 21, wherein the activator switch is configured to be closed when the activator element is in the activation position, wherein closing the activation switch completes a power circuit to the monitoring circuit so as to activate the monitoring circuit.*

*24. The assembly of claim 21, further comprising a communication circuit operably arranged to receive and transmit data to external data handling sources.*

*25. The assembly of claim 21, wherein the displacement of the activator element from the initial position to the activation position is indicative of an initiation of an injection.*

*26. The assembly of claim 21, wherein the drive element comprises a spring.*

*27. The assembly of claim 21, wherein the monitoring unit further comprises a second activator switch.*

* * * * *